US009701722B2

(12) United States Patent
Rao et al.

(10) Patent No.: US 9,701,722 B2
(45) Date of Patent: Jul. 11, 2017

(54) DESIGNING A SOLUBLE FULL-LENGTH HIV-1 GP41 TRIMER

(71) Applicant: The Catholic University of America, Washington, DC (US)

(72) Inventors: Venigalla B. Rao, Silver Spring, MD (US); Guofen Gao, Washington, DC (US)

(73) Assignee: The Catholic University of America, Washington, DC (US)

( * ) Notice: Subject to any disclaimer, the term of this patent is extended or adjusted under 35 U.S.C. 154(b) by 0 days.

(21) Appl. No.: 15/080,804

(22) Filed: Mar. 25, 2016

(65) Prior Publication Data

US 2016/0207964 A1 Jul. 21, 2016

Related U.S. Application Data

(62) Division of application No. 14/091,401, filed on Nov. 27, 2013, now Pat. No. 9,328,145.

(60) Provisional application No. 61/731,147, filed on Nov. 29, 2012.

(51) Int. Cl.
*C07K 14/05* (2006.01)
*C07K 14/005* (2006.01)
*C12N 7/02* (2006.01)
*C12N 7/00* (2006.01)

(52) U.S. Cl.
CPC ............. *C07K 14/005* (2013.01); *C12N 7/00* (2013.01); *C12N 7/02* (2013.01); *C07K 2319/35* (2013.01); *C07K 2319/70* (2013.01); *C07K 2319/735* (2013.01); *C12N 2740/16122* (2013.01); *C12N 2740/16222* (2013.01); *C12N 2795/10122* (2013.01); *C12N 2795/10123* (2013.01)

(58) Field of Classification Search
CPC .. C12N 7/02; C12N 7/00; C12N 2740/16122; C07K 2319/35; C07K 2319/70; C07K 2319/735
See application file for complete search history.

(56) References Cited

PUBLICATIONS

Gao, G., et al., Jan. 2013, Designing a soluble near full-length HIV-1 gp41 trimer, J. Biol. Chem. 288(1):234-246.*
Search Report received in European Patent Application No. 13858143.4, mailed May 20, 2016.
Gao et al., "Designing a Soluble Near Full-Length HIV-1 gp41 Trimer", The Journal of Biological Chemistry, vol. 288, No. 1, pp. 234-246 (2013).
Meier et al., "Foldon, the Natural Trimerization Domain of T4 Fibritin, Dissociates into a Monomeric A-state Form containing a Stable B-Hairpin: Atomic Details of Trimer Dissaciation and Local B-Hairpin Stability from Residual Dipolar Couplings", J. Mol. Biol., 344, pp. 1051-1069 (2004).
Qiao et al., "Design, Expression, and Immunogenicity of a Soluble HIV Trimeric Envelope Fragment Adopting a Prefusion gp41 Configuration", The Journal of Biological Chemistry, vol. 280, No. 24, pp. 23188-23149 (2006).
Sathaliyawala, T., Rao, M., Maclean, D. M., Birx, D. L., Alving, C. R., and Rao, V. B. (2006) Assembly of human immunodeficiency virus (HIV) antigens on bacteriophage T4: a novel in vitro approach to construct multicomponent HIV vaccines. J Virol 80, 7688-7698.
Greenberg, M., Cammack, N., Salgo, M., and Smiley, L. (2004) HIV fusion and its inhibition in antiretroviral therapy. Rev Med Virol 14, 321-337.
Meadows, D. C., and Gervay-Hague, J. (2006) Current developments in HIV chemotherapy. ChemMedChem 1, 16-29.
Geijtenbeek, T. B., Krooshoop, D. J., Bleijs, D. A., van Vliet, S. J., van Duijnhoven, G. C., Grabovsky, V., Alon, R., Figdor, C. G., and van Kooyk, Y. (2000) DC-SIGN-ICAM-2 interaction mediates dendritic cell trafficking. Nat Immunol 1, 353-357.
Dalgleish, A. G., Beverley, P. C., Clapham, P. R., Crawford, D. H., Greaves, M. F., and Weiss, R. A. (1984) The CD4 (T4) antigen is an essential component of the receptor for the AIDS retrovirus. Nature 312, 763-767.
Horton, R. M., Hunt, H. D., Ho, S. N., Pullen, J. K., and Pease, L. R. (1989) Engineering hybrid genes without the use of restriction enzymes: gene splicing by overlap extension. Gene 77, 61-68.
Montefiori, D. C. (2009) Measuring HIV neutralization in a luciferase reporter gene assay. Methods Mol Biol 485, 395-405.
Phogat, S., and Wyatt, R. (2007) Rational modifications of HIV-1 envelope glycoproteins for immunogen design. Curr Pharm Des 13, 213-227.
Chan, D. C., and Kim, P. S. (1998) HIV entry and its inhibition. Cell 93, 681-684.
Maltez, F., Doroana, M., Branco, T., and Valente, C. (2011) Recent advances in antiretroviral treatment and prevention in HIV-infected patients. Curr Opin HIV AIDS 6 Suppl 1, S21-30.
Wyatt, R., and Sodroski, J. (1998) The HIV-1 envelope glycoproteins: fusogens, antigens, and immunogens. Science 280, 1884-1888.
Furuta, R. A., Wild, C. T., Weng, Y., and Weiss, C. D. (1998) Capture of an early fusion-active conformation of HIV-1 gp41. Nat Struct Biol 5, 276-279.
Weissenhorn, W., Dessen, A., Harrison, S. C., Skehel, J. J., and Wiley, D. C. (1997) Atomic structure of the ectodomain from HIV-1 gp41. Nature 387, 426-430.

(Continued)

*Primary Examiner* — Jeffrey Parkin
(74) *Attorney, Agent, or Firm* — Miles & Stockbridge P.C.; Ajay A. Jagtiani

(57) ABSTRACT

Described herein is a soluble HIV-1 retrovirus transmembrane glycoprotein gp41 trimer (Soc-gp41M-Fd) containing a partial ectodomain and the cytoplasmic domain, that is fused to the small outer capsid (Soc) protein of bacteriophage T4 and the Foldon domain of the bacteriophage T4 fibritin (Fd). The gp41 trimer that has a prehairpin structure could be utilized to understand the mechanism of viral entry and as a candidate for development of HIV-1 vaccines, diagnostics and therapeutics. Other secondary embodiments of the gp41 proteins containing different modifications are also disclosed. According to one embodiment, the gp41 trimer is further attached to a cell penetration peptide (CPP). Methods of producing gp41 trimers are also disclosed.

5 Claims, 11 Drawing Sheets

(56) References Cited

PUBLICATIONS

Scholz, C., Schaarschmidt, P., Engel, A. M., Andres, H., Schmitt, U., Faatz, E., Balbach, J., and Schmid, F. X. (2005) Functional solubilization of aggregation-prone HIV envelope proteins by covalent fusion with chaperone modules. J Mol Biol 345, 1229-1241.

Lorizate, M., Gomara, M. J., de la Torre, B. G., Andreu, D., and Nieva, J. L. (2006) Membrane-transferring sequences of the HIV-1 Gp41 ectodomain assemble into an immunogenic complex. J Mol Biol 360, 45-55.

Tsumoto, K., Umetsu, M., Kumagai, I., Ejima, D., Philo, J. S., and Arakawa, T. (2004) Role of arginine in protein refolding, solubilization, and purification. Biotechnol Prog 20, 1301-1308.

Li, Q., Shivachandra, S. B., Leppla, S. H., and Rao, V. B. (2006) Bacteriophage T4 capsid: a unique platform for efficient surface assembly of macromolecular complexes. J Mol Biol 363, 577-588.

Gao et al., Designing a Soluble Near Full-length HIV-1 gp41 Trimer, The Journal of Biological Chemistry, vol. 288, No. 1, pp. 234-246 (2013).

Rerks-Ngarm, S., Pitisuttithum, P., Nitayaphan, S., Kaewkungwal, J., Chiu, J., Paris, R., Premsri, N., Namwat, C., de Souza, M., Adams, E., Benenson, M., Gurunathan, S., Tartaglia, J., McNeil, J. G., Francis, D. P., Stablein, D., Birx, D. L., Chunsuttiwat, S., Khamboonruang, C., Thongcharoen, P., Robb, M. L., Michael, N. L., Kunasol, P., and Kim, J. H. (2009) Vaccination with ALVAC and AIDSVAX to prevent HIV-1 infection in Thailand. N Engl J Med 361, 2209-2220.

Burton, D. R., Poignard, P., Stanfield, R. L., and Wilson, I. A. (2012) Broadly neutralizing antibodies present new prospects to counter highly antigenically diverse viruses. Science 337, 183-186.

Boutwell, C. L., Rolland, M. M., Herbeck, J. T., Mullins, J. I., and Allen, T. M. (2010) Viral evolution and escape during acute HIV-1 infection. J Infect Dis 202 Suppl 2, S309-314.

Pejchal, R., and Wilson, I. A. (2010) Structure-based vaccine design in HIV: blind men and the elephant? Curr Pharm Des 16, 3744-3753.

Arthos, J., Cicala, C., Martinelli, E., Macleod, K., Van Ryk, D., Wei, D., Xiao, Z., Veenstra, T. D.,Conrad, T. P., Lempicki, R. A., McLaughlin, S., Pascuccio, M., Gopaul, R., McNally, J., Cruz, C. C., Censoplano, N., Chung, E., Reitano, K. N., Kottilil, S., Goode, D. J., and Fauci, A. S. (2008) HIV-1 envelope protein binds to and signals through integrin alpha4beta7, the gut mucosal homing receptor for peripheral T cells. Nat Immunol 9, 301-309.

Cicala, C., Martinelli, E., McNally, J. P., Goode, D. J., Gopaul, R., Hiatt, J., Jelicic, K., Kottilil, S., Macleod, K., O'Shea, A., Patel, N., Van Ryk, D., Wei, D., Pascuccio, M., Yi, L., McKinnon, L., Izulla, P., Kimani, J., Kaul, R., Fauci, A. S., and Arthos, J. (2009) The integrin alpha4beta7 forms a complex with cell-surface CD4 and defines a T-cell subset that is highly susceptible to infection by HIV-1. Proc Natl Acad Sci U S A 106, 20877-20882.

Berger, E. A., Murphy, P. M., and Farber, J. M. (1999) Chemokine receptors as HIV-1 coreceptors: roles in viral entry, tropism, and disease. Annu Rev Immunol 17, 657-700.

Colman, P. M., and Lawrence, M. C. (2003) The structural biology of type I viral membrane fusion. Nat Rev Mol Cell Biol 4, 309-319.

Muster, T., Steindl, F., Purtscher, M., Trkola, A., Klima, A., Himmler, G., Ruker, F., and Katinger, H. (1993) A conserved neutralizing epitope on gp41 of human immunodeficiency virus type 1. J Virol 67, 6642-6647.

Barbato, G., Bianchi, E., Ingallinella, P., Humi, W. H., Miller, M. D., Ciliberto, G., Cortese, R., Bazzo, R., Shiver, J. W., and Pessi, A. (2003) Structural analysis of the epitope of the anti-HIV antibody 2F5 sheds light into its mechanism of neutralization and HIV fusion. J Mol Biol 330, 1101-1115.

Brunel, F. M., Zwick, M. B., Cardoso, R. M., Nelson, J. D., Wilson, I. A., Burton, D. R., and Dawson, P. E. (2006) Structure-function analysis of the epitope for 4E10, a broadly neutralizing human immunodeficiency virus type 1 antibody. J Virol 80, 1680-1687.

Nelson, J. D., Kinkead, H., Brunel, F. M., Leaman, D., Jensen, R., Louis, J. M., Maruyama, T., Bewley, C. A., Bowdish, K., Clore, G. M., Dawson, P. E., Frederickson, S., Mage, R. G., Richman, D. D., Burton, D. R., and Zwick, M. B. (2008) Antibody elicited against the gp41 N-heptad repeat (NHR) coiled-coil can neutralize HIV-1 with modest potency but non-neutralizing antibodies also bind to NHR mimetics. Virology 377, 170-183.

Chakrabarti, B. K., Walker, L. M., Guenaga, J. F., Ghobbeh, A., Poignard, P., Burton, D. R., and Wyatt, R. T. (2011) Direct antibody access to the HIV-1 membrane-proximal external region positively correlates with neutralization sensitivity. J Virol 85, 8217-8226.

Qin, L., Fokine, A., O'Donnell, E., Rao, V. B., and Rossmann, M. G. (2009) (2010) Structure of the small outer capsid protein, Soc: a clamp for stabilizing capsids of T4-like phages. J Mol Biol 395, 728-741.

Polonis, V. R., Brown, B. K., Rosa Borges, A., Zolla-Pazner, S., Dimitrov, D. S., Zhang, M. Y., Barnett, S. W., Ruprecht, R. M., Scarlatti, G., Fenyo, E. M., Montefiori, D. C., McCutchan, F. E., and Michael, N. L. (2008) Recent advances in the characterization of HIV-1 neutralization assays for standardized evaluation of the antibody response to infection and vaccination. Virology 375, 315-320.

Pancera, M., Majeed, S., Ban, Y. E., Chen, L., Huang, C. C., Kong, L., Kwon, Y. D., Stuckey, J., Zhou, T., Robinson, J. E., Schief, W. R., Sodroski, J., Wyatt, R., and Kwong, P. D. (2010) Structure of HIV-1 gp120 with gp41-interactive region reveals layered envelope architecture and basis of conformational mobility. Proc Natl Acad Sci U S A 107, 1166-1171.

Robinson, W. E., Jr., Gorny, M. K., Xu, J. Y., Mitchell, W. M., and Zolla-Pazner, S. (1991) Two immunodominant domains of gp41 bind antibodies which enhance human immunodeficiency virus type 1 infection in vitro. J Virol 65, 4169-4176.

Robinson, W. E., Jr., Kawamura, T., Lake, D., Masuho, Y., Mitchell, W. M., and Hersh, E. M. (1990) Antibodies to the primary immunodominant domain of human immunodeficiency virus type 1 (HIV-1) glycoprotein gp41 enhance HIV-1 infection in vitro. J Virol 64, 5301-5305.

Pantophlet, R., and Burton, D. R. (2006) GP120: target for neutralizing HIV-1 antibodies. Annu Rev Immunol 24, 739-769.

Peachman, K. K., Li, Q., Matyas, G. R., Shivachandra, S. B., Lovchik, J., Lyons, R. C., Alving, C. R., Rao, V. B., and Rao, M. (2011) Anthrax vaccine antigen-adjuvant formulations completely protect New Zealand white rabbits against challenge with Bacillus anthracis Ames strain spores. Clin Vaccine Immunol 19, 11-16.

Barouch, D. H., Liu, J., Li, H., Maxfield, L. F., Abbink, P., Lynch, D. M., Iampietro, M. J., SanMiguel, A., Seaman, M. S., Ferrari, G., Forthal, D. N., Ourmanov, I., Hirsch, V. M., Carville, A., Mansfield, K. G., Stablein, D., Pau, M. G., Schuitemaker, H., Sadoff, J. C., Billings, E. A., Rao, M., Robb, M. L., Kim, J. H., Marovich, M. A., Goudsmit, J., and Michael, N. L. (2012) Vaccine protection against acquisition of neutralization-resistant SIV challenges in rhesus monkeys. Nature 482, 89-93.

Qin, L., Shivachandra, S. B., Leppla, S. H., and Rao, V. B., (2006) Bacteriophage T4 capsid: a unique platform for efficient surface assembly of macromolecular complexes. J. Mol Biol 363, 577-588.

Walker, L. M., Huber, M., Doores, K. J., Falkowska, E., Pejchal, R., Julien, J. P., Wang, S. K., Ramos, A., Chan-Hui, P. Y., Moyle, M., Mitcham, J. L., Hammond, P. W., Olsen, O. A., Phung, P., Fling, S., Wong, C. H., Phogat, S., Wrin, T., Simek, M. D., Koff, W C., Wilson, I. A., Burton, D. R., and Poignard, P. (2011) Broad neutralization coverage of HIV by multiple highly potent antibodies. Nature 477, 466-470.

Kwong, P. D., Mascola, J. R., and Nabel, G. J. (2012) Rational Design of Vaccines to Elicit Broadly Neutralizing Antibodies to HIV-1. Cold Spring Harbor Perspectives in Biology 4.

McElrath, M. J., and Haynes, B. F. (2010) Induction of immunity to human immunodeficiency virus type-1 by vaccination. Immunity 33, 542-554.

Melikyan, G. B., Markosyan, R. M., Hemmati, H., Delmedico, M. K., Lambert, D. M., and Cohen, F. S. (2000) Evidence that the transition of HIV-1 gp41 into a six-helix bundle, not the bundle configuration, induces membrane fusion. J Cell Biol 151, 413-423.

Walker, L. M., and Burton, D. R. (2010) Rational antibody-based HIV-1 vaccine design: current approaches and future directions. Curr Opin Immunol 22, 358-366.

(56) References Cited

OTHER PUBLICATIONS

Zwick, M. B., Labrijn, A. F., Wang, M., Spenlehauer, C., Saphire, E. O., Binley, J. M., Moore, J. P., Stiegler, G., Katinger, H., Burton, D. R., and Parren, P. W. (2001) Broadly neutralizing antibodies targeted to the membrane-proximal external region of human immunodeficiency virus type 1 glycoprotein gp41. J Virol 75, 10892-10905.

Hessell, A. J., Rakasz, E. G., Tehrani, D. M., Huber, M., Weisgrau, K. L., Landucci, G., Forthal, D. N., Koff, W. C., Poignard, P., Watkins, D. I., and Burton, D. R. (2009) Broadly neutralizing monoclonal antibodies 2F5 and 4E10 directed against the human immunodeficiency virus type 1 gp41 membrane-proximal external region protect against mucosal challenge by simian-human immunodeficiency virus SHIVBa-L. J Virol 84, 1302-1313.

Mascola, J. R., Lewis, M. G., Stiegler, G., Harris, D., VanCott, T. C., Hayes, D., Louder, M. K., Brown, C. R., Sapan, C. V., Frankel, S. S., Lu, Y., Robb, M. L., Katinger, H., and Birx, D. L. (1999) Protection of Macaques against pathogenic simian/human immunodeficiency virus 89.6PD by passive transfer of neutralizing antibodies. J Virol 73, 4009-4018.

Mascola, J. R., Stiegler, G., VanCott, T. C., Katinger, H., Carpenter, C. B., Hanson, C. E., Beary, H., Hayes, D., Frankel, S. S., Birx, D. L., and Lewis, M. G. (2000) Protection of macaques against vaginal transmission of a pathogenic HIV-1/SIV chimeric virus by passive infusion of neutralizing antibodies. Nat Med 6, 207-210.

Frey, G., Chen, J., Rits-Volloch, S., Freeman, M. M., Zolla-Pazner, S., and Chen, B. (2010) Distinct conformational states of HIV-1 gp41 are recognized by neutralizing and non-neutralizing antibodies. Nat Struct Mol Biol 17, 1486-1491.

Frey, G., Peng, H., Rits-Volloch, S., Morelli, M., Cheng, Y., and Chen, B. (2008) A fusion-intermediate state of HIV-1 gp41 targeted by broadly neutralizing antibodies. Proc Natl Acad Sci U S A 105, 3739-3744.

Montero, M., van Houten, N. E., Wang, X., and Scott, J. K. (2008) The membrane-proximal external region of the human immunodeficiency virus type 1 envelope: dominant site of antibody neutralization and target for vaccine design. Microbiol Mol Biol Rev 72, 54-84.

Chan, D. C., Fass, D., Berger, J. M., and Kim, P. S. (1997) Core structure of gp41 from the HIV envelope glycoprotein. Cell 89, 263-273.

de Rosny, E., Vassell, R., Jiang, S., Kunert, R., and Weiss, C. D. (2004) Binding of the 2F5 monoclonal antibody to native and fusion-intermediate forms of human immunodeficiency virus type 1 gp41: implications for fusion-inducing conformational changes. J Virol 78, 2627-2631.

Wang, J., Tong, P., Lu, L., Zhou, L., Xu, L., Jiang, S., and Chen, Y. H. (2011) HIV-1 gp41 core with exposed membrane-proximal external region inducing broad HIV-1 neutralizing antibodies. PLoS One 6, e18233.

Kim, M., Qiao, Z., Yu, J., Montefiori, D., and Reinherz, E. L. (2007) Immunogenicity of recombinant human immunodeficiency virus type 1-like particles expressing gp41 derivatives in a pre-fusion state. Vaccine 25, 5102-5114.

Hager-Braun, C., Katinger, H., and Tomer, K. B. (2006) The HIV-neutralizing monoclonal antibody 4E10 recognizes N-terminal sequences on the native antigen. J Immunol 176, 7471-7481.

Yang, X., Lee, J., Mahony, E. M., Kwong, P. D., Wyatt, R., and Sodroski, J. (2002) Highly stable trimers formed by human immunodeficiency virus type 1 envelope glycoproteins fused with the trimeric motif of T4 bacteriophage fibritin. J Virol 76, 4634-4642.

Li, Q., Shivachandra, S. B., Zhang, Z., and Rao, V. B. (2007) Assembly of the small outer capsid protein, Soc, on bacteriophage T4: a novel system for high density display of multiple large anthrax toxins and foreign proteins on phage capsid. J Mol Biol 370, 1006-1019.

Gnann, J. W., Jr., Nelson, J. A., and Oldstone, M. B. (1987) Fine mapping of an immunodominant domain in the transmembrane glycoprotein of human immunodeficiency virus. J Virol 61, 2639-2641.

Mathiesen, T., Chiodi, F., Broliden, P. A., Albert, J., Houghten, R. A., Utter, G., Wahren, B., and Norrby, E. (1989) Analysis of a subclass-restricted HIV-1 gp41 epitope by omission peptides. Immunology 67, 1-7.

Wang, J. J., Steel, S., Wisniewolski, R., and Wang, C. Y. (1986) Detection of antibodies to human T-lymphotropic virus type III by using a synthetic peptide of 21 amino acid residues corresponding to a highly antigenic segment of gp41 envelope protein. Proc Natl Acad Sci U S A 83, 6159-6163.

Tran, E. E., Borgnia, M. J., Kuybeda, O., Schauder, D. M., Bartesaghi, A., Frank, G. A., Sapiro, G., Milne, J. L., and Subramaniam, S. (2012) Structural Mechanism of Trimeric HIV-1 Envelope Glycoprotein Activation. PLoS Pathog 8, e1002797.

Finnegan, C. M., Berg, W., Lewis, G. K., and DeVico, A. L. (2002) Antigenic properties of the human immunodeficiency virus transmembrane glycoprotein during cell-cell fusion. J Virol 76, 12123-12134.

Heitz, F., Morris, M. C., and Divita, G. (2009) Twenty years of cell-penetrating peptides: from molecular mechanisms to therapeutics. Br J Pharmacol 157, 195-206.

Melchers, M., Matthews, K., de Vries, R. P., Eggink, D., van Montfort, T., Bontjer, I., van de Sandt, C., David, K., Berkhout, B., Moore, J. P., and Sanders, R. W. (2011) A stabilized HIV-1 envelope glycoprotein trimer fused to CD40 ligand targets and activates dendritic cells. Retrovirology 8, 48.

Wei, X., Decker, J. M., Wang, S., Hui, H., Kappes, J. C., Wu, X., Salazar-Gonzalez, J. F., Salazar, M. G., Kilby, J. M., Saag, M. S., Komarova, N. L., Nowak, M. A., Hahn, B. H., Kwong, P. D., and Shaw, G. M. (2003) Antibody neutralization and escape by HIV-1. Nature 422, 307-312.

Bianchi, E., Joyce, J. G., Miller, M. D., Finnefrock, A. C., Liang, X., Finotto, M., Ingallinella, P., McKenna, P., Citron, M., Ottinger, E., Hepler, R. W., Hrin, R., Nahas, D., Wu, C., Montefiori, D., Shiver, J. W., Pessi, A., and Kim, P. S. (2010) Vaccination with peptide mimetics of the gp41 prehairpin fusion intermediate yields neutralizing antisera against HIV-1 isolates. Proc Natl Acad Sci U S A 107, 10655-10660.

* cited by examiner

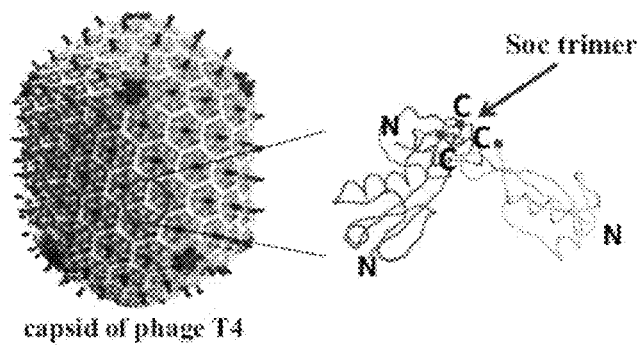
FIG. 7A
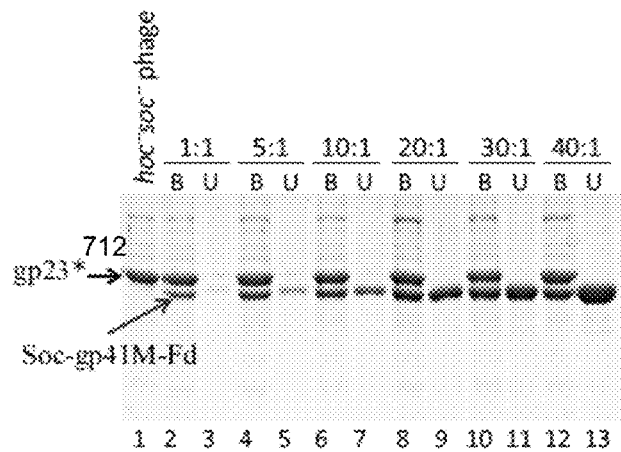 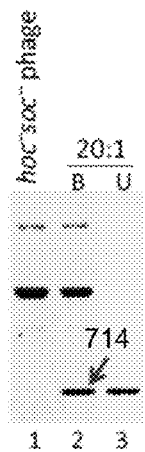 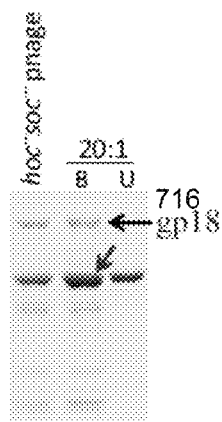
FIG. 7B  FIG. 7C  FIG. 7D

| Soc fusions | $B_{max}$ | $K_d$ |
|---|---|---|
| Soc | 870 | 75 |
| Soc-gp41M-Fd | 859 | 121 |
| Soc-gp41ectoM-Fd | 928 | 156 |
| CPP-Soc-gp41M-Fd | 794 | 143 |

SEQUENCE LISTING

```
<160> NUMBER OF SEQ ID NOS: 14

<210> SEQ ID NO 1
<211> LENGTH: 346
<212> TYPE: PRT
<213> ORGANISM: Human immunodeficiency virus

<400> SEQUENCE: 1

Met Ala Val Gly Ile Gly Ala Leu Phe Leu Gly Phe Leu Gly Ala Ala
1               5                   10                  15

Gly Ser Thr Met Gly Ala Ala Ser Met Thr Leu Thr Val Gln Ala Arg
            20                  25                  30

Gln Leu Leu Ser Gly Ile Val Gln Gln Asn Asn Leu Leu Arg Ala
        35                  40                  45

Ile Glu Ala Gln Gln His Leu Leu Gln Leu Thr Val Trp Gly Ile Lys
    50                  55                  60
```

Gln Leu Gln Ala Arg Ile Leu Ala Val Glu Arg Tyr Leu Lys Asp Gln
65                  70                  75                  80

Gln Leu Leu Gly Ile Trp Gly Cys Ser Gly Lys Leu Ile Cys Thr Thr
                85                  90                  95

Ala Val Pro Trp Asn Ala Ser Trp Ser Asn Lys Ser Leu Glu Gln Ile
            100                 105                 110

Trp Asn His Thr Thr Trp Met Glu Trp Asp Arg Glu Ile Asn Asn Tyr
            115                 120                 125

Thr Ser Leu Ile His Ser Leu Ile Glu Glu Ser Gln Asn Gln Gln Glu
        130                 135                 140

Lys Asn Glu Gln Glu Leu Leu Glu Leu Asp Lys Trp Ala Ser Leu Trp
145                 150                 155                 160

Asn Trp Phe Asn Ile Thr Asn Trp Leu Trp Tyr Ile Lys Leu Phe Ile
                165                 170                 175

Met Ile Val Gly Gly Leu Val Gly Leu Arg Ile Val Phe Ala Val Leu
            180                 185                 190

Ser Ile Val Asn Arg Val Arg Gln Gly Tyr Ser Pro Leu Ser Phe Gln
        195                 200                 205

Thr His Leu Pro Thr Pro Arg Gly Pro Asp Arg Pro Glu Gly Ile Glu
    210                 215                 220

Glu Glu Gly Gly Glu Arg Asp Arg Asp Arg Ser Ile Arg Leu Val Asn
225                 230                 235                 240

Gly Ser Leu Ala Leu Ile Trp Asp Asp Leu Arg Ser Leu Cys Leu Phe
                245                 250                 255

Ser Tyr His Arg Leu Arg Asp Leu Leu Leu Ile Val Thr Arg Ile Val
            260                 265                 270

Glu Leu Leu Gly Arg Arg Gly Trp Glu Ala Leu Lys Tyr Trp Trp Asn
        275                 280                 285

Leu Leu Gln Tyr Trp Ser Gln Glu Leu Lys Asn Ser Ala Val Ser Leu
    290                 295                 300

Leu Asn Ala Thr Ala Ile Ala Val Ala Glu Gly Thr Asp Arg Val Ile
305                 310                 315                 320

Glu Val Val Gln Gly Ala Cys Arg Ala Ile Arg His Ile Pro Arg Arg
                325                 330                 335

Ile Arg Gln Gly Leu Glu Arg Ile Leu Leu
            340                 345

<210> SEQ ID NO 2
<211> LENGTH: 79
<212> TYPE: PRT
<213> ORGANISM: bacteriophage T4

<400> SEQUENCE: 2

Met Ala Gly Gly Tyr Val Asn Ile Lys Thr Phe Thr His Pro Ala Gly
1               5                   10                  15

Glu Gly Lys Glu Val Lys Gly Met Glu Val Ser Val Pro Phe Glu Ile
            20                  25                  30

Tyr Ser Asn Glu His Arg Ile Ala Asp Ala His Tyr Gln Thr Phe Pro
        35                  40                  45

Ser Glu Lys Ala Ala Tyr Thr Thr Val Val Thr Asp Ala Ala Asp Trp
    50                  55                  60

Arg Thr Lys Asn Ala Ala Met Phe Thr Pro Thr Pro Val Ser Gly
65                  70                  75

```
<210> SEQ ID NO 3
<211> LENGTH: 419
<212> TYPE: PRT
<213> ORGANISM: Artificial Sequence
<220> FEATURE:
<223> OTHER INFORMATION: Soc-gp41

<400> SEQUENCE: 3

Met Ala Gly Gly Tyr Val Asn Ile Lys Thr Phe Thr His Pro Ala Gly
1               5                   10                  15

Glu Gly Lys Glu Val Lys Gly Met Glu Val Ser Val Pro Phe Glu Ile
                20                  25                  30

Tyr Ser Asn Glu His Arg Ile Ala Asp Ala His Tyr Gln Thr Phe Pro
            35                  40                  45

Ser Glu Lys Ala Ala Tyr Thr Thr Val Val Thr Asp Ala Ala Asp Trp
        50                  55                  60

Arg Thr Lys Asn Ala Ala Met Phe Thr Pro Thr Pro Val Ser Gly Ser
65                  70                  75                  80

Ala Ser Ala Met Ala Val Gly Ile Gly Ala Leu Phe Leu Gly Phe Leu
                85                  90                  95

Gly Ala Ala Gly Ser Thr Met Gly Ala Ala Ser Met Thr Leu Thr Val
                100                 105                 110

Gln Ala Arg Gln Leu Leu Ser Gly Ile Val Gln Gln Asn Asn Leu
            115                 120                 125

Leu Arg Ala Ile Glu Ala Gln Gln His Leu Leu Gln Leu Thr Val Trp
        130                 135                 140

Gly Ile Lys Gln Leu Gln Ala Arg Ile Leu Ala Val Glu Arg Tyr Leu
145                 150                 155                 160

Lys Asp Gln Gln Leu Leu Gly Ile Trp Gly Cys Ser Gly Lys Leu Ile
                165                 170                 175

Cys Thr Thr Ala Val Pro Trp Asn Ala Ser Trp Ser Asn Lys Ser Leu
            180                 185                 190

Glu Gln Ile Trp Asn His Thr Thr Trp Met Glu Trp Asp Arg Glu Ile
        195                 200                 205

Asn Asn Tyr Thr Ser Leu Ile His Ser Leu Ile Glu Glu Ser Gln Asn
    210                 215                 220

Gln Gln Glu Lys Asn Glu Gln Glu Leu Leu Glu Leu Asp Lys Trp Ala
225                 230                 235                 240

Ser Leu Trp Asn Trp Phe Asn Ile Thr Asn Trp Leu Trp Tyr Ile Lys
                245                 250                 255

Lys Lys Asn Arg Val Arg Gln Gly Tyr Ser Pro Leu Ser Phe Gln Thr
            260                 265                 270

His Leu Pro Thr Pro Arg Gly Pro Asp Arg Pro Glu Gly Ile Glu Glu
        275                 280                 285

Glu Gly Gly Glu Arg Asp Arg Asp Arg Ser Ile Arg Leu Val Asn Gly
    290                 295                 300

Ser Leu Ala Leu Ile Trp Asp Asp Leu Arg Ser Leu Cys Leu Phe Ser
305                 310                 315                 320

Tyr His Arg Leu Arg Asp Leu Leu Leu Ile Val Thr Arg Ile Val Glu
                325                 330                 335

Leu Leu Gly Arg Arg Gly Trp Glu Ala Leu Lys Tyr Trp Trp Asn Leu
            340                 345                 350

Leu Gln Tyr Trp Ser Gln Glu Leu Lys Asn Ser Ala Val Ser Leu Leu
        355                 360                 365

Asn Ala Thr Ala Ile Ala Val Ala Glu Gly Thr Asp Arg Val Ile Glu
```

```
              370                 375                 380
Val Val Gln Gly Ala Cys Arg Ala Ile Arg His Ile Pro Arg Arg Ile
385                 390                 395                 400

Arg Gln Gly Leu Glu Arg Ile Leu Leu Leu Glu His His His His
                405                 410                 415

His His His

<210> SEQ ID NO 4
<211> LENGTH: 389
<212> TYPE: PRT
<213> ORGANISM: Artificial Sequence
<220> FEATURE:
<223> OTHER INFORMATION: Soc-gp41-deltaID

<400> SEQUENCE: 4

Met Ala Gly Gly Tyr Val Asn Ile Lys Thr Phe Thr His Pro Ala Gly
1               5                   10                  15

Glu Gly Lys Glu Val Lys Gly Met Glu Val Ser Val Pro Phe Glu Ile
                20                  25                  30

Tyr Ser Asn Glu His Arg Ile Ala Asp Ala His Tyr Gln Thr Phe Pro
            35                  40                  45

Ser Glu Lys Ala Ala Tyr Thr Thr Val Val Thr Asp Ala Ala Asp Trp
50                  55                  60

Arg Thr Lys Asn Ala Ala Met Phe Thr Pro Thr Pro Val Ser Gly Ser
65                  70                  75                  80

Ala Ser Ala Ala Val Gly Ile Gly Ala Leu Phe Leu Gly Phe Leu Gly
                85                  90                  95

Ala Ala Gly Ser Thr Met Gly Ala Ala Ser Met Thr Leu Thr Val Gln
                100                 105                 110

Ala Arg Gln Leu Leu Ser Gly Ile Val Gln Gln Gln Asn Asn Leu Leu
                115                 120                 125

Arg Ala Ile Glu Ala Gln Gln His Leu Leu Gln Leu Thr Val Trp Gly
            130                 135                 140

Ile Lys Gln Leu Thr Ala Val Pro Trp Asn Ala Ser Trp Ser Asn Lys
145                 150                 155                 160

Ser Leu Glu Gln Ile Trp Asn His Thr Thr Trp Met Glu Trp Asp Arg
                165                 170                 175

Glu Ile Asn Asn Tyr Thr Ser Leu Ile His Ser Leu Ile Glu Glu Ser
                180                 185                 190

Gln Asn Gln Gln Glu Lys Asn Glu Gln Glu Leu Leu Glu Leu Asp Lys
            195                 200                 205

Trp Ala Ser Leu Trp Asn Trp Phe Asn Ile Thr Asn Trp Leu Trp Tyr
210                 215                 220

Ile Lys Lys Lys Asn Arg Val Arg Gln Gly Tyr Ser Pro Leu Ser Phe
225                 230                 235                 240

Gln Thr His Leu Pro Thr Pro Arg Gly Pro Asp Arg Pro Glu Gly Ile
                245                 250                 255

Glu Glu Glu Gly Gly Glu Arg Asp Arg Asp Arg Ser Ile Arg Leu Val
                260                 265                 270

Asn Gly Ser Leu Ala Leu Ile Trp Asp Asp Leu Arg Ser Leu Cys Leu
            275                 280                 285

Phe Ser Tyr His Arg Leu Arg Asp Leu Leu Leu Ile Val Thr Arg Ile
            290                 295                 300

Val Glu Leu Leu Gly Arg Arg Gly Trp Glu Ala Leu Lys Tyr Trp Trp
305                 310                 315                 320
```

Asn Leu Leu Gln Tyr Trp Ser Gln Glu Leu Lys Asn Ser Ala Val Ser
            325                 330                 335

Leu Leu Asn Ala Thr Ala Ile Ala Val Ala Glu Gly Thr Asp Arg Val
            340                 345                 350

Ile Glu Val Val Gln Gly Ala Cys Arg Ala Ile Arg His Ile Pro Arg
            355                 360                 365

Arg Ile Arg Gln Gly Leu Glu Arg Ile Leu Leu Glu His His His
            370                 375                 380

His His His His His
385

<210> SEQ ID NO 5
<211> LENGTH: 389
<212> TYPE: PRT
<213> ORGANISM: Artificial Sequence
<220> FEATURE:
<223> OTHER INFORMATION: Soc-gp41M

<400> SEQUENCE: 5

Met Ala Gly Gly Tyr Val Asn Ile Lys Thr Phe Thr His Pro Ala Gly
1               5                   10                  15

Glu Gly Lys Glu Val Lys Gly Met Glu Val Ser Val Pro Phe Glu Ile
            20                  25                  30

Tyr Ser Asn Glu His Arg Ile Ala Asp Ala His Tyr Gln Thr Phe Pro
        35                  40                  45

Ser Glu Lys Ala Ala Tyr Thr Thr Val Val Thr Asp Ala Ala Asp Trp
    50                  55                  60

Arg Thr Lys Asn Ala Ala Met Phe Thr Pro Thr Pro Val Ser Gly Ser
65                  70                  75                  80

Ala Ser Ala Ala Val Gly Ile Gly Ala Leu Phe Leu Gly Phe Leu Gly
                85                  90                  95

Ala Ala Gly Ser Thr Met Gly Ala Ala Ser Met Thr Leu Thr Val Gln
            100                 105                 110

Ala Arg Gln Leu Leu Ser Gly Ile Val Gln Gln Gln Glu Asn Leu Leu
        115                 120                 125

Glu Ala Ile Glu Ala Gln Gln His Arg Leu Gln Asn Thr Val Trp Gly
    130                 135                 140

Ile Lys Gln Leu Thr Ala Val Pro Trp Asn Ala Ser Trp Ser Asn Lys
145                 150                 155                 160

Ser Leu Glu Gln Ile Trp Asn His Thr Thr Trp Met Glu Trp Asp Arg
                165                 170                 175

Glu Glu Asn Asn Tyr Thr Ser Leu Ile His Ser Glu Ile Glu Glu Ser
            180                 185                 190

Gln Asn Gln Gln Glu Lys Asn Glu Gln Glu Leu Leu Glu Leu Asp Lys
        195                 200                 205

Trp Ala Ser Leu Trp Asn Trp Phe Asn Ile Thr Asn Trp Leu Trp Tyr
    210                 215                 220

Ile Lys Lys Lys Asn Arg Val Arg Gln Gly Tyr Ser Pro Leu Ser Phe
225                 230                 235                 240

Gln Thr His Leu Pro Thr Pro Arg Gly Pro Asp Arg Pro Glu Gly Ile
                245                 250                 255

Glu Glu Glu Gly Gly Glu Arg Asp Arg Asp Arg Ser Ile Arg Leu Val
            260                 265                 270

Asn Gly Ser Leu Ala Leu Ile Trp Asp Asp Leu Arg Ser Leu Cys Leu
        275                 280                 285

```
Phe Ser Tyr His Arg Leu Arg Asp Leu Leu Leu Ile Val Thr Arg Ile
    290                 295                 300

Val Glu Leu Leu Gly Arg Arg Gly Trp Glu Ala Leu Lys Tyr Trp Trp
305                 310                 315                 320

Asn Leu Leu Gln Tyr Trp Ser Gln Glu Leu Lys Asn Ser Ala Val Ser
                325                 330                 335

Leu Leu Asn Ala Thr Ala Ile Ala Val Ala Glu Gly Thr Asp Arg Val
            340                 345                 350

Ile Glu Val Val Gln Gly Ala Cys Arg Ala Ile Arg His Ile Pro Arg
        355                 360                 365

Arg Ile Arg Gln Gly Leu Glu Arg Ile Leu Leu Glu His His His
    370                 375                 380

His His His His His
385

<210> SEQ ID NO 6
<211> LENGTH: 420
<212> TYPE: PRT
<213> ORGANISM: Artificial Sequence
<220> FEATURE:
<223> OTHER INFORMATION: Soc-gp41M-Fd

<400> SEQUENCE: 6

Met Ala Gly Gly Tyr Val Asn Ile Lys Thr Phe Thr His Pro Ala Gly
1               5                   10                  15

Glu Gly Lys Glu Val Lys Gly Met Glu Val Ser Val Pro Phe Glu Ile
            20                  25                  30

Tyr Ser Asn Glu His Arg Ile Ala Asp Ala His Tyr Gln Thr Phe Pro
        35                  40                  45

Ser Glu Lys Ala Ala Tyr Thr Thr Val Val Thr Asp Ala Ala Asp Trp
    50                  55                  60

Arg Thr Lys Asn Ala Ala Met Phe Thr Pro Thr Pro Val Ser Gly Ser
65                  70                  75                  80

Ala Ser Ala Ala Val Gly Ile Gly Ala Leu Phe Leu Gly Phe Leu Gly
                85                  90                  95

Ala Ala Gly Ser Thr Met Gly Ala Ala Ser Met Thr Leu Thr Val Gln
            100                 105                 110

Ala Arg Gln Leu Leu Ser Gly Ile Val Gln Gln Gln Glu Asn Leu Leu
        115                 120                 125

Glu Ala Ile Glu Ala Gln Gln His Arg Leu Gln Asn Thr Val Trp Gly
    130                 135                 140

Ile Lys Gln Leu Thr Ala Val Pro Trp Asn Ala Ser Trp Ser Asn Lys
145                 150                 155                 160

Ser Leu Glu Gln Ile Trp Asn His Thr Thr Trp Met Glu Trp Asp Arg
                165                 170                 175

Glu Glu Asn Asn Tyr Thr Ser Leu Ile His Ser Glu Ile Glu Glu Ser
            180                 185                 190

Gln Asn Gln Gln Glu Lys Asn Glu Gln Glu Leu Leu Glu Leu Asp Lys
        195                 200                 205

Trp Ala Ser Leu Trp Asn Trp Phe Asn Ile Thr Asn Trp Leu Trp Tyr
    210                 215                 220

Ile Lys Lys Lys Asn Arg Val Arg Gln Gly Tyr Ser Pro Leu Ser Phe
225                 230                 235                 240

Gln Thr His Leu Pro Thr Pro Arg Gly Pro Asp Arg Pro Glu Gly Ile
                245                 250                 255
```

Glu Glu Glu Gly Gly Glu Arg Asp Arg Asp Arg Ser Ile Arg Leu Val
                260                 265                 270

Asn Gly Ser Leu Ala Leu Ile Trp Asp Asp Leu Arg Ser Leu Cys Leu
            275                 280                 285

Phe Ser Tyr His Arg Leu Arg Asp Leu Leu Ile Val Thr Arg Ile
290                 295                 300

Val Glu Leu Leu Gly Arg Arg Gly Trp Glu Ala Leu Lys Tyr Trp Trp
305                 310                 315                 320

Asn Leu Leu Gln Tyr Trp Ser Gln Glu Leu Lys Asn Ser Ala Val Ser
                325                 330                 335

Leu Leu Asn Ala Thr Ala Ile Ala Val Ala Glu Gly Thr Asp Arg Val
            340                 345                 350

Ile Glu Val Val Gln Gly Ala Cys Arg Ala Ile Arg His Ile Pro Arg
            355                 360                 365

Arg Ile Arg Gln Gly Leu Glu Arg Ile Leu Leu Ser Ala Ser Ala Gly
            370                 375                 380

Tyr Ile Pro Glu Ala Pro Arg Asp Gly Gln Ala Tyr Val Arg Lys Asp
385                 390                 395                 400

Gly Glu Trp Val Leu Leu Ser Thr Phe Leu Leu Glu His His His His
                405                 410                 415

His His His His
        420

<210> SEQ ID NO 7
<211> LENGTH: 267
<212> TYPE: PRT
<213> ORGANISM: Artificial Sequence
<220> FEATURE:
<223> OTHER INFORMATION: Soc-gp41ectoM-Fd

<400> SEQUENCE: 7

Met Ala Gly Gly Tyr Val Asn Ile Lys Thr Phe Thr His Pro Ala Gly
1               5                   10                  15

Glu Gly Lys Glu Val Lys Gly Met Glu Val Ser Val Pro Phe Glu Ile
                20                  25                  30

Tyr Ser Asn Glu His Arg Ile Ala Asp Ala His Tyr Gln Thr Phe Pro
            35                  40                  45

Ser Glu Lys Ala Ala Tyr Thr Thr Val Val Thr Asp Ala Ala Asp Trp
        50                  55                  60

Arg Thr Lys Asn Ala Ala Met Phe Thr Pro Thr Pro Val Ser Gly Ser
65                  70                  75                  80

Ala Ser Ala Ala Val Gly Ile Gly Ala Leu Phe Leu Gly Phe Leu Gly
                85                  90                  95

Ala Ala Gly Ser Thr Met Gly Ala Ala Ser Met Thr Leu Thr Val Gln
            100                 105                 110

Ala Arg Gln Leu Leu Ser Gly Ile Val Gln Gln Gln Asn Asn Leu Leu
        115                 120                 125

Glu Ala Ile Glu Ala Gln Gln His Arg Leu Gln Asn Thr Val Trp Gly
130                 135                 140

Ile Lys Gln Leu Thr Ala Val Pro Trp Asn Ala Ser Trp Ser Asn Lys
145                 150                 155                 160

Ser Leu Glu Gln Ile Trp Asn His Thr Thr Trp Met Glu Trp Asp Arg
                165                 170                 175

Glu Glu Asn Asn Tyr Thr Ser Leu Ile His Ser Glu Ile Glu Glu Ser
            180                 185                 190

```
Gln Asn Gln Gln Glu Lys Asn Glu Gln Glu Leu Leu Glu Leu Asp Lys
            195                 200                 205

Trp Ala Ser Leu Trp Asn Trp Phe Asn Ile Thr Asn Trp Leu Trp Tyr
        210                 215                 220

Ile Lys Ser Ala Ser Ala Gly Tyr Ile Pro Glu Ala Pro Arg Asp Gly
225                 230                 235                 240

Gln Ala Tyr Val Arg Lys Asp Gly Glu Trp Val Leu Leu Ser Thr Phe
            245                 250                 255

Leu Leu Glu His His His His His His His His
            260                 265

<210> SEQ ID NO 8
<211> LENGTH: 13
<212> TYPE: PRT
<213> ORGANISM: Artificial Sequence
<220> FEATURE:
<223> OTHER INFORMATION: Synthetic peptide sequence derived from HIV-1

<400> SEQUENCE: 8

Asn Gly Tyr Gly Arg Lys Lys Arg Arg Gln Arg Arg Arg
1               5                   10

<210> SEQ ID NO 9
<211> LENGTH: 446
<212> TYPE: PRT
<213> ORGANISM: Artificial Sequence
<220> FEATURE:
<223> OTHER INFORMATION: CPP-Soc-gp41M-Fd

<400> SEQUENCE: 9

Asn Gly Tyr Gly Arg Lys Lys Arg Arg Gln Arg Arg Arg Gly Gly Ser
1               5                   10                  15

Gly Gly Ser Gly Gly Ser Gly Gly Ser Gly Met Ala Gly Gly Tyr Val
            20                  25                  30

Asn Ile Lys Thr Phe Thr His Pro Ala Gly Glu Gly Lys Glu Val Lys
        35                  40                  45

Gly Met Glu Val Ser Val Pro Phe Glu Ile Tyr Ser Asn Glu His Arg
50                  55                  60

Ile Ala Asp Ala His Tyr Gln Thr Phe Pro Ser Glu Lys Ala Ala Tyr
65                  70                  75                  80

Thr Thr Val Val Thr Asp Ala Ala Asp Trp Arg Thr Lys Asn Ala Ala
            85                  90                  95

Met Phe Thr Pro Thr Pro Val Ser Gly Ser Ala Ser Ala Ala Val Gly
            100                 105                 110

Ile Gly Ala Leu Phe Leu Gly Phe Leu Gly Ala Ala Gly Ser Thr Met
            115                 120                 125

Gly Ala Ala Ser Met Thr Leu Thr Val Gln Ala Arg Gln Leu Leu Ser
130                 135                 140

Gly Ile Val Gln Gln Gln Glu Asn Leu Leu Glu Ala Ile Glu Ala Gln
145                 150                 155                 160

Gln His Arg Leu Gln Asn Thr Val Trp Gly Ile Lys Gln Leu Thr Ala
            165                 170                 175

Val Pro Trp Asn Ala Ser Trp Ser Asn Lys Ser Leu Glu Gln Ile Trp
            180                 185                 190

Asn His Thr Thr Trp Met Glu Trp Asp Arg Glu Glu Asn Asn Tyr Thr
            195                 200                 205

Ser Leu Ile His Ser Glu Ile Glu Glu Ser Gln Asn Gln Gln Glu Lys
```

```
                210                 215                 220
Asn Glu Gln Glu Leu Leu Glu Leu Asp Lys Trp Ala Ser Leu Trp Asn
225                 230                 235                 240

Trp Phe Asn Ile Thr Asn Trp Leu Trp Tyr Ile Lys Lys Lys Asn Arg
                245                 250                 255

Val Arg Gln Gly Tyr Ser Pro Leu Ser Phe Gln Thr His Leu Pro Thr
            260                 265                 270

Pro Arg Gly Pro Asp Arg Pro Glu Gly Ile Glu Glu Gly Gly Glu
        275                 280                 285

Arg Asp Arg Asp Arg Ser Ile Arg Leu Val Asn Gly Ser Leu Ala Leu
        290                 295                 300

Ile Trp Asp Asp Leu Arg Ser Leu Cys Leu Phe Ser Tyr His Arg Leu
305                 310                 315                 320

Arg Asp Leu Leu Leu Ile Val Thr Arg Ile Val Glu Leu Leu Gly Arg
                325                 330                 335

Arg Gly Trp Glu Ala Leu Lys Tyr Trp Trp Asn Leu Leu Gln Tyr Trp
            340                 345                 350

Ser Gln Glu Leu Lys Asn Ser Ala Val Ser Leu Leu Asn Ala Thr Ala
        355                 360                 365

Ile Ala Val Ala Glu Gly Thr Asp Arg Val Ile Glu Val Val Gln Gly
        370                 375                 380

Ala Cys Arg Ala Ile Arg His Ile Pro Arg Arg Ile Arg Gln Gly Leu
385                 390                 395                 400

Glu Arg Ile Leu Leu Ser Ala Ser Ala Gly Tyr Ile Pro Glu Ala Pro
                405                 410                 415

Arg Asp Gly Gln Ala Tyr Val Arg Lys Asp Gly Glu Trp Val Leu Leu
            420                 425                 430

Ser Thr Phe Leu Leu Glu His His His His His His
        435                 440                 445

<210> SEQ ID NO 10
<211> LENGTH: 4
<212> TYPE: PRT
<213> ORGANISM: Artificial Sequence
<220> FEATURE:
<223> OTHER INFORMATION: Linker

<400> SEQUENCE: 10

Ser Ala Ser Ala
1

<210> SEQ ID NO 11
<211> LENGTH: 27
<212> TYPE: PRT
<213> ORGANISM: Artificial Sequence
<220> FEATURE:
<223> OTHER INFORMATION: Synthetic peptide sequence derived from
    bacteriophage T4.

<400> SEQUENCE: 11

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 12
<211> LENGTH: 23
<212> TYPE: PRT
<213> ORGANISM: Artificial Sequence
```

```
<220> FEATURE:
<223> OTHER INFORMATION: Synthetic peptide sequence derived from an
      HIV-1 virus

<400> SEQUENCE: 12

Leu Glu Leu Asp Lys Trp Ala Ser Leu Trp Asn Trp Phe Asn Ile Thr
1               5                   10                  15

Asn Trp Leu Trp Tyr Ile Lys
            20

<210> SEQ ID NO 13
<211> LENGTH: 23
<212> TYPE: PRT
<213> ORGANISM: Artificial Sequence
<220> FEATURE:
<223> OTHER INFORMATION: Synthetic peptide sequence derived from an
      HIV-1 virus

<400> SEQUENCE: 13

Leu Ser Ile Asn Glu Ala Phe Lys Trp Leu Asp Trp Trp Thr Leu Asn
1               5                   10                  15

Asp Leu Trp Tyr Ile Trp Lys
            20

<210> SEQ ID NO 14
<211> LENGTH: 13
<212> TYPE: PRT
<213> ORGANISM: Artificial Sequence
<220> FEATURE:
<223> OTHER INFORMATION: CPP-Tat

<400> SEQUENCE: 14

Pro Gly Arg Lys Lys Arg Arg Gln Arg Arg Pro Pro Gln
1               5                   10
```

DESIGNING A SOLUBLE FULL-LENGTH HIV-1 GP41 TRIMER

CROSS-REFERENCE TO RELATED APPLICATIONS

This application claims benefit of priority to U.S. Provisional Patent Application No. 61/731,147 filed Nov. 29, 2012, entitled "DESIGNING A SOLUBLE FULL-LENGTH HIV-1 GP41 TRIMER" which is incorporated by reference in its entirety.

This application makes reference to U.S. Provisional Patent Application No. 61/322,334, entitled "PROTEIN AND NUCLEIC ACID DELIVERY VEHICLES, COMPONENTS AND MECHANISMS THEREOF", filed Apr. 9, 2010 and U.S. patent application Ser. No. 13/082,466, filed Apr. 8, 2011, entitled "PROTEIN AND NUCLEIC ACID DELIVERY VEHICLES, COMPONENTS AND MECHANISMS THEREOF", which is incorporated herein by reference in its entirety.

BACKGROUND

Field of the Invention

This present invention relates to a soluble human retrovirus HIV-1 glycoprotein gp41 trimer to help understand the detailed entry mechanism of the virus into a host cell, and as a candidate for development of HIV-1 vaccines, diagnostics and therapeutics.

Related Art

Although the basic pathway of HIV-1 entry has been established, the detailed mechanism that involves a series of initial interactions between the virus and host cell receptors, extracellular glycoprotein gp120 and transmembrane glycoprotein gp41 as well as their intermediates, is poorly understood. Thus, design of gp41 recombinants that mimic key intermediates is essential to elucidate the mechanism as well as to develop potent therapeutics and vaccines. Standard approaches to produce such recombinants have not been successful because of the extreme hydrophobicity of gp41. The present application overcomes the shortcomings of the prior art as described herein.

SUMMARY

According to a first broad aspect, the present invention provides a soluble HIV-1 retrovirus transmembrane glycoprotein gp41 trimer (Soc-gp41M-Fd) containing a partial ectodomain and the cytoplasmic domain, that is fused to the small outer capsid (Soc) protein of bacteriophage T4 and the Foldon domain of the bacteriophage T4 fibritin (Fd).

According to a second broad aspect, the present invention provides a soluble HIV-1 retrovirus transmembrane glycoprotein gp41 trimer (Soc-gp41M-Fd) containing a partial ectodomain and the cytoplasmic domain, that is fused to the small outer capsid (Soc) protein of bacteriophage T4 and the Foldon domain of the bacteriophage T4 fibritin (Fd), and further attached to a cell penetration peptide (CPP). Methods of producing gp41 trimers are also disclosed.

According to a third broad aspect, the present invention provides a protein comprising the amino acid sequence as shown in SEQ ID NO: 6.

According to a fourth broad aspect, the present invention provides a method comprising the following steps: (a) expressing a fusion protein from an expression vector containing a DNA fragment encoding a fusion protein comprising amino acid sequence SEQ ID NO: 6, (b) purifying the fusion protein from step (a) to thereby form a fusion protein in purified form comprising amino acid sequence SEQ ID NO: 6.

According to a third broad aspect, the present invention provides a protein comprising the amino acid sequence as shown in SEQ ID NO: 5.

According to a third broad aspect, the present invention provides a protein comprising the amino acid sequence as shown in SEQ ID NO: 4.

According to a third broad aspect, the present invention provides a protein comprising the amino acid sequence as shown in SEQ ID NO: 3.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 7A is a diagram showing the Cryo-EM structure of phage T4 capsid.

FIG. 7B is an image of an SDS-PAGE gel illustrating the binding of Soc-gp41M-Fd on phage T4.

FIG. 7C is an image of an SDS-PAGE gel illustrating the binding of Soc-gp41ectoM-Fd on phage T4 at a Soc-fusion protein to capsid binding sites ratio of 20:1.

FIG. 7D is an image of an SDS-PAGE gel illustrating the binding of CPP-Soc-gp41M-Fd on phage T4 at a Soc-fusion protein to capsid binding sites ratio of 20:1.

DETAILED DESCRIPTION OF THE PREFERRED EMBODIMENTS

Definitions

Figure 1A:
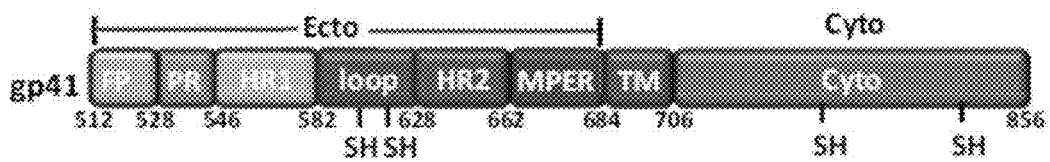
FIG. 1A is a schematic representation of various regions of gp41.

Where the definition of terms departs from the commonly used meaning of the term, applicant intends to utilize the definitions provided below, unless specifically indicated.

For purposes of the present invention, it should be noted that the singular forms, "a," "an" and "the" include reference to the plural unless the context as herein presented clearly indicates otherwise.

For purposes of the present invention, the term "amino acid" refers to a biological organic compound that is coded for by a genetic code of an organism and is a precursor to protein.

For purposes of the present invention, the term "cloning compatible ends" refers to blunt or sticky ends of a DNA fragment cleaved by restriction enzymes (or restriction endonucleases) that cleave DNA at specific recognition sites comprising specific nucleotide sequences. To be able to clone a DNA insert into a cloning or expression vector, both ends of the DNA insert have to be treated with restriction enzymes that create compatible ends to ensure that the DNA insert is incorporated in the right orientation.

For purposes of the present invention, the term "deletion" refers to the absence of an amino acid residue from the polypeptide sequence of a mutant protein.

For purposes of the present invention, the term "fusion protein" refers to a protein created through the joining of two or more genes which originally coded for separate proteins. Translation of this fusion gene results in a single polypeptide with functional properties derived from each of the original proteins.

For purposes of the present invention, the terms "identical" or "identity" refer to the percentage of amino acid residues of two or more polypeptide sequences having the same amino acid at corresponding positions. For example, a protein that is at least 90% identical to a polypeptide sequence will have at least 90% of its residues that are the same as those in the amino acid sequence at corresponding positions For purposes of the present invention, the term "mutant protein" refers to the protein product encoded by a gene with mutation.

For purposes of the present invention, the term "mutation" refers to a change in the polypeptide sequence of a protein.

For purposes of the present invention, the term "overlap extension PCR" or "overlap extension polymerase chain reaction" refers a molecular biology technique that is a variation of the traditional PCR technique that is used to create long DNA fragments from shorter ones.

For purposes of the present invention, the term "PAGE" refers to polyacrylamide gel electrophoresis, a technique to separate macromolecules, usually proteins or nucleic acids, according to their electrophoretic mobility.

For purposes of the present invention, the term "recombinant" refers to any nucleic acid, protein or biological molecule that is produced via a genetic recombination process.

For purposes of the present invention, the term "substitution" refers to the replacement of an amino acid residue at a specific position along the polypeptide sequence of a mutant protein.

For purposes of the present invention, the term "transformant" refers to a prokaryotic cell that has been genetically altered through uptake of foreign DNA.

For purposes of the present invention, the term "trimer" refers to a protein complex formed by three usually non-convalently bound protein macromolecules.

For purposes of the present invention, the term "vector" refers to a DNA molecule used as a vehicle to artificially carry foreign genetic material into another cell, where it can be replicated and/or expressed.

DESCRIPTION

The HIV-1 envelope spike is a trimer of heterodimers composed of an external glycoprotein gp120 and a transmembrane glycoprotein gp41. gp120 initiates virus entry by binding to host receptors whereas gp41 mediates fusion between viral and host membranes. Although the basic pathway of HIV-1 entry is established, the detailed mechanism is poorly understood. Design of gp41 recombinants that mimic key intermediates is essential to elucidate the mechanism as well as to develop potent therapeutics and vaccines. Standard approaches to produce such recombinants have not been successful because of the extreme hydrophobicity of gp41. Here, using molecular genetics and biochemical approaches, a series of hypotheses were tested to design soluble full-length gp41 trimers. The two long heptad repeat helices HR1 and HR2 of gp41 ectodomain that precede the membrane proximal external region were mutated to disrupt intra-molecular HR1-HR2 interactions but not the inter-molecular HR1-HR1 interactions. This resulted in reduced aggregation and improved solubility. Attachment of a 27-amino acid foldon at the C-terminus and slow refolding channeled gp41 into trimers. The trimers are stabilized in a prehairpin structure, as evident from binding of a HR2 peptide to the exposed HR1 grooves and inhibition of virus neutralization by the broadly neutralizing antibodies, 2F5 and 4E10. Attachment to phage T4 small outer capsid protein converted gp41 trimers into nanoparticle arrays. These approaches for the first time led to the design of a soluble gp41 trimer containing both the fusion peptide and the cytoplasmic domain, providing new insights into the mechanism and development of gp41-based HIV-1 vaccines.

Acquired immunodeficiency syndrome (AIDS) caused by the human immunodeficiency virus type 1 (HIV-1) is a major global health epidemic. Although effective chemotherapeutics have been discovered, these inhibit virus replication after infection has already occurred (1, 2). A preventative vaccine that can block HIV-1 entry at the site of infection is probably the best strategy to control the epidemic (3-5). Of the four large vaccine efficacy trials conducted in humans so far, only the RV144 trial showed a modest but significant protection (31.2%) from HIV-1 infection (6). Development of an effective HIV-1 vaccine remains as one of the biggest challenges, mainly because of the extreme genetic diversity of HIV-1 (7). Coupled with this diversity are the masking of essential epitopes by glycosylation and the extraordinary evolution of viral envelope to evade host immune responses (8). A major goal of HIV-1 vaccine development, therefore, is to understand the entry mechanism in detail and identify conserved intermediates that could serve as immunogens as well as targets for therapeutics and antibodies (Abs) that can block virus entry (4, 9).

Figure 1B:
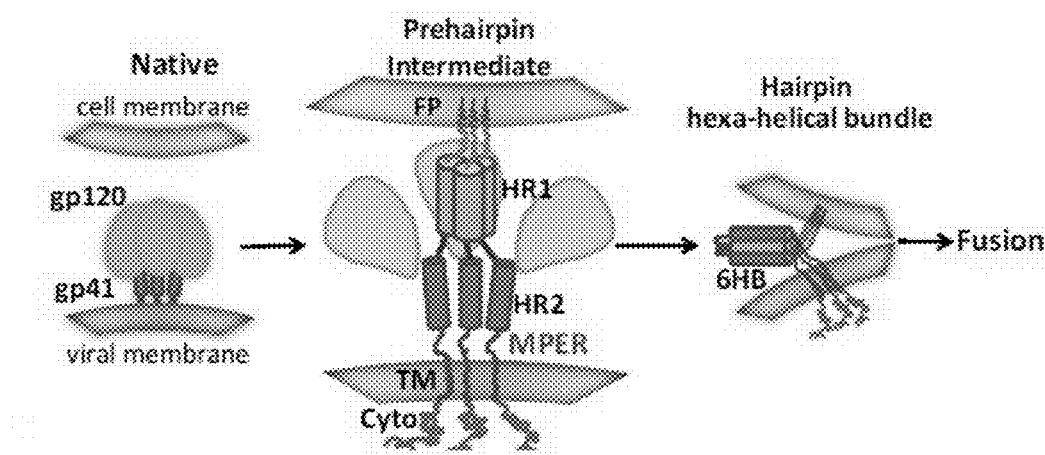
FIG. 1B is a schematic diagram of HIV-1 entry with emphasis on gp41 function.

HIV-1, a "spherical" enveloped retrovirus, fuses with the plasma membrane of a host cell and delivers the nucleocapsid core into the cytosol. A key component of entry is the trimeric spike embedded in the lipid bilayer of the viral envelope. It is a trimer of heterodimers, each dimer consisting of an extracellular glycoprotein gp120 and a transmembrane glycoprotein gp41 that are derived from proteolytic cleavage of the precursor protein gp160 (10). HIV-1 entry involves a series of initial interactions between the virus and host cell receptors. The virus is first captured through relatively weak interactions between gp120 and surface molecules, such as $\alpha_4\beta_7$ integrin and DC-SIGN (11-13), which then leads to high affinity interactions with CD4, the primary receptor on $CD4^+$ T cell (14). A conformational change in gp120 exposes the binding site for the chemokine co-receptor, CCR5 or CXCR4 (15). Further conformational changes lead to the opening up of gp41's two long helices containing heptad repeat (HR) sequences HR1 and HR2 and insertion of the N-terminal fusion peptide into the host cell membrane (16, 17). A prehairpin intermediate, a three-stranded coiled coil stabilized by inter-molecular interactions between HR1 helices, is formed (FIGS. 1A and 1B). In FIG. 1A, FP is fusion peptide; PR is fusion peptide proximal region; HR1 is heptad repeat 1; loop (118) is apical loop; HR2 is heptad repeat 2; MPER is membrane proximal external region; TM is transmembrane helix; Cyto is cytoplasmic domain. Ecto and Cyto correspond to ectomain and cytoplasmic domains, respectively. Numbers correspond to the first amino acid for each region using the gp41 sequence from HIV-1 strain HXB2. Positions of the four cysteines (—SH) are shown.

Following the interaction of HIV-1 envelope with the host receptors, as shown in FIG. 1B, gp120 and gp41 undergo conformational changes resulting in the exposure of HR1 and HR2 helices and formation of a prehairpin intermediate. The HR2 helix loops back and interacts with the groove between HR1 helices forming a hexa-helical bundle (6HB), bringing the viral and cellular membranes to close proximity for fusion.

gp120 subunits dissociate allowing the HR2 helices at the base of the spike to fold back and interact with the HR1 helices. The hexa-helical bundle thus formed brings the host and viral membranes in close proximity facilitating membrane fusion and release of the nucleocapsid core into the cytosol (18-20).

Understanding the structure and function of the intermediates is essential to design immunogen mimics that induce broadly neutralizing antibodies (bnAbs) against genetically diverse HIV-1 viruses (4, 21, 22). In fact, the conserved membrane proximal external region (MPER), which is present at the base of the spike between the HR2 helices and the transmembrane domain (FIG. 1B), consists of epitopes that are recognized by a series of bnAbs, 2F5 and 4E10 being the most well-characterized among them (23-26). Passive immunization with these bnAbs reduced viremia in HIV-1 infected individuals and nonhuman primates (27-29). The MPER epitopes are well exposed in the prehairpin intermediate (FIG. 1B), the most extended conformation of gp41 ectodomain, making it as a prime target for immunogen design (30-32).

Although the crystal structure of the hexa-helical bundle intermediate (see FIGS. 1B and 3A), the core of fusion-active gp41, has been determined (33), very little is known about the structure and function of the prehairpin intermediate (31, 34, 35). In FIG. 3A, 312, 314, 316 are HR1 helices whereas 322, 324, 326 are HR2 helices. Side chains are shown as sticks. Attempts to produce any form of full-length gp41 in a soluble, trimeric state have not been successful because of the unusually high hydrophobicity of gp41 and its extreme propensity to precipitate (36). Only certain truncated or structurally constrained versions of gp41 ectodomain, containing only HR1, HR2, and MPER motifs, have been produced but these induce either weak or no bnAbs (31, 36-39). Other components of the gp41 molecule, such as the fusion peptide and the cytoplasmic domain might be necessary to generate a structure that mimics the native prehairpin intermediate, displaying the MPER and other functional motifs in the right conformation (40, 41). However, there have been no reports of soluble, structurally-defined, gp41 oligomers containing the fusion peptide and/or cytoplasmic domain.

Disclosed embodiments of this present invention report the design of full-length soluble gp41 recombinants containing the fusion peptide, the ectodomain, and the cytoplasmic domain. Designs of the disclosed embodiments may include introduction of mutations that weaken intra-molecular interactions between HR1 and HR2 helices while retaining inter-molecular interactions between HR1 helices. Such mutations minimized nonspecific interactions and improved the solubility of gp41. Attachment of foldon, a phage T4 trimerization tag along with slow refolding led to folding of gp41 protein into trimers and defined oligomers. These gp41 trimers were displayed on bacteriophage T4 capsid nanoparticles by attaching to the small outer capsid protein (Soc), which also forms trimers by binding to the quasi-3-fold axes of the virus capsid (42). These gp41 recombinants potently inhibited HIV-1 virus neutralization by 2F5 and 4E10 mAbs, presumably by competing with the prehairpin structure formed during virus entry. These approaches have led to the design of soluble full-length, gp41 trimers in a prehairpin-like structure that for the first time could be utilized to understand the mechanism of viral entry and as a candidate for development of HIV-1 vaccines, diagnostics, and therapeutics.

EXAMPLES

Example 1

Construction of the Expression Vectors

All the gp41 constructs were generated by splicing-by-overlap extension PCR using wild-type HXB2 gp41 DNA as a template (43). Mutations were introduced using primers containing the desired mutations in the nucleotide sequence. For construction of gp41 fusion recombinants, the DNA fragments corresponding to gp41, Soc, and foldon were amplified by PCR using the respective DNA templates and overlapping primers containing additional amino acids SASA as a linker between each fragment. The fragments were then stitched together and the stitched DNA was amplified using the end primers containing unique restriction sites, Xho I or Nco I. The final PCR product was digested with Xho I and Nco I and ligated with the linearized and dephosphorylated pTriEx-4 Neo plasmid vector. The recombinant DNA was transformed into E. coli XL-10 Gold competent cells, and miniprep plasmid DNA was prepared from individual colonies. The presence of DNA insert was identified by restriction digestion and/or amplification with insert-specific primers. The accuracy of the cloned DNA was confirmed by DNA sequencing. The plasmids were then transformed into E. coli BL21 (DE3) RIPL competent cells for protein expression.

Example 2

Expression and Solubility Testing of gp41 Recombinant Proteins

BL21 (DE3) RIPL cells containing gp41 clones were induced with 1 mM IPTG at 30° C. for 3 h. The cells were lysed using bacterial protein extraction reagent B-PER and centrifuged at 12,000 g for 10 min. The soluble supernatant and insoluble pellet fractions were analyzed by SDS-PAGE. The pellets containing the insoluble inclusion bodies were treated with different denaturing reagents, SDS, urea, or guanidine hydrochloride (GnHCl). After centrifugation at 12,000 g for 10 min, the supernatants and pellets were analyzed by SDS-PAGE.

Example 3

Purification of Recombinant Proteins

The cells after IPTG induction were harvested by centrifugation at 8,200 g for 15 min at 4° C. and lysed using an Aminco French press. The inclusion bodies containing the gp41 recombinant protein were separated from the soluble fraction by centrifugation at 34,000 g for 20 min. The inclusion bodies pellet from 1 L culture was dissolved in 50 ml of 50 mM Tris-HCl (pH 8), 300 mM NaCl, and 20 mM imidazole buffer containing 8 M urea. After 30 min, the sample was centrifuged at 34,000 g for 20 min to remove cell debris. The supernatant was loaded onto a HisTrap HP column pre-equilibrated with the same buffer. The bound protein was eluted with 20-500 mM linear imidazole gradient in the same buffer. A slow refolding procedure was performed to refold the purified protein. The protein was further purified by Superdex 200 gel filtration chromatography (Hiload prep grade) in 20 mM Tris-HCl (pH 8) and 100 mM NaCl buffer. For the gp41 recombinants expressed as soluble proteins, the supernatant of cell lysate was purified by Histrap and Superdex 200 gel filtration columns. The purified proteins were stored frozen at −80° C.

Example 4

Refolding of gp41 Recombinants

Following purification by HisTrap chromatography in 8 M urea, the protein was refolded by slow dialysis with incrementally decreasing the urea concentration (6 M, 4 M, 2 M, 1 M, 0.5 M, or no urea). The dialysis buffer in addition contained 20 mM Tris-HCl (pH 8), 100 mM NaCl, 200 mM L-Arg, and 5 mM DTT. Protein was dialyzed for at least 8 h before changing to another buffer with decreasing concentration of urea. At the last step, the protein was dialyzed against either 20 mM Tris-HCl (pH 8) and 100 mM NaCl buffer, or PBS (pH 7.4), for 6 hours and the buffer was changed every 2 hours.

Example 5

SDS-Polyacrylamide Gel Electrophoresis (PAGE) and Native PAGE

Twelve percent SDS-Polyacrylamide gel was used to determine the expression, solubility, and purification quality of gp41 recombinant proteins. The proteins were stained with Coomassie Blue R-250 Native-PAGE (4-20% gradient gels) was used to determine the folding and oligomeric states of the recombinant proteins. The proteins were stained with Bio-safe Coomassie Stain.

Example 6

Pseudovirus Neutralization Competition Assay

TZM/bl cells were used to determine HIV-1 neutralization by 2F5 and 4E10 mAbs. The mAb was titered in 3-fold serial dilutions starting at 50 µg/ml in the growth medium [DMEM with 100 U/ml penicillin, 100 µg/ml streptomycin, 2 mM L-glutamine and 15% fetal calf serum. On a 96-well flat-bottom black plate, 12.5 µl of the mAb at different dilutions was mixed with 12.5 µl of gp41 recombinant proteins or other control competitors at a concentration of 120 nM for 2F5 neutralization, and 200 nM for 4E10 neutralization. The samples were incubated for 30 min at 37° C. and 25 µl of pseudovirus SF162 at a dilution optimized to yield 150,000 relative luminescence units (RLUs) was added. Samples were incubated for an additional 30 min. TZM/bl cells (50 µl; $2 \times 10^5$ cells/ml in growth medium containing 60 µg/ml DEAE-dextran) was added to each well. Each plate included wells with cells and pseudovirus (virus control) or cells alone (background control). The assay was also performed by omitting the first incubation of gp41 with 2F5 or 4E10. The plates were incubated for 48 h, and then 100 µl/well of reconstituted Brite Lite Plus was added. The RLUs were measured using a Victor 2 luminometer. The percent inhibition due to the presence of the mAb was calculated by comparing RLU values from wells containing mAb to well with virus control. IC50 was calculated for each mAb alone and mAb pre-mixed with gp41 recombinant proteins or other control competitors. Two independent assays were performed and the results were averaged (44, 45).

Example 7

In Vitro Display of Soc-gp41 Trimers on Phage T4 Capsid hoc⁻soc⁻ phage was purified by velocity sucrose gradient centrifugation. About $2 \times 10^{10}$ PFU of purified hoc⁻soc⁻ phage were centrifuged in 1.5 ml LoBind Eppendorf tubes at 18,000 g, 4° C. for 45 min. The pellets were resuspended in 10 μl PBS buffer. Purified Soc-gp41 fusion proteins were added at the desired concentration and the reaction mixture (100 μl) was incubated at 4° C. for 45 min. Phage was sedimented by centrifugation as described above, and the pellets were washed twice with 1 ml PBS and resuspended in 10 to 20 μl of the same buffer. The sample was transferred to a fresh Eppendorf tube and analyzed by SDS-PAGE. The density volumes of bound and unbound proteins were determined by laser densitometry. The copy number of displayed gp41 was calculated in reference to the known copy number of the major capsid protein gp23* (930 copies per phage) ("*" represents the cleaved form of the major capsid protein gp23) or the tail sheath protein gp18 (138 copies per phage) in the respective lane. The data were plotted as one site saturation ligand binding curve and fitted by non-linear regression using the SigmaPlot10.0 software.

Results gp41 Recombinant Design

The design of gp41 recombinant proteins has been proven to be challenging for several reasons. First, gp41 (SEQ ID NO: 1) structure is stabilized by interactions with gp120 in the native envelope trimer (46). Separation from gp120 leads to exposure of highly hydrophobic regions such as fusion peptide, HR1 and HR2 helices, and MPER (FIG. 1A). Nonspecific high-avidity interactions between these regions during heterologous protein expression lead to aggregation of nascent polypeptide chains. Second, a series of interacting residues (hydrophobic and charged) of HR1 and HR2 helices (see FIG. 3A) favor combinatorial, rather than unique, interactions among the polypeptide chains (33). Third, gp41 contains four cysteines (FIG. 1A), which can form nonspecific crosslinks, especially in an aggregated state where the tightly packed polypeptide chains exclude water. These problems may be addressed by rational modification of gp41 sequence and structure by: i) introduction of mutations, ii) attachment of tag, and iii) controlling folding kinetics (FIG. 1C), as described in this present invention.

Mutations—

Figure 3A:
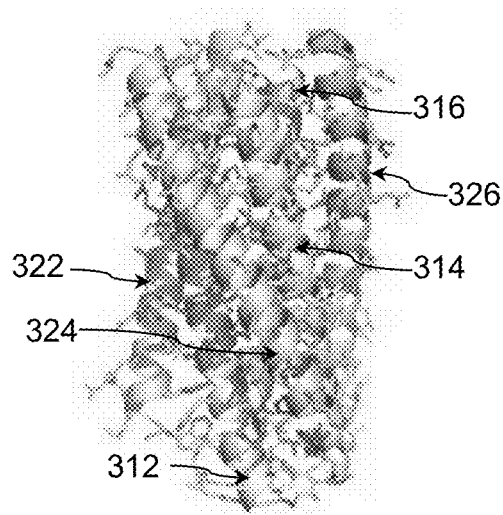
FIG. 3A is a ribbon diagram showing the gp41 6HB structure (PDB ID: 1AIK).
Figure 3B:
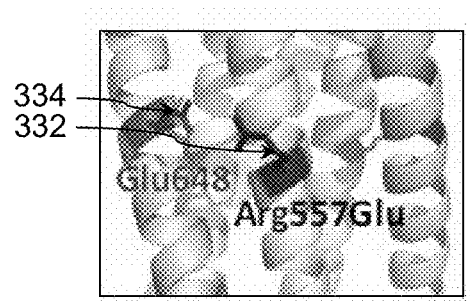
FIG. 3B is a ribbon diagram illustrating the change of the residue Arg557 of HR1 into Glu557.
Figure 3C:
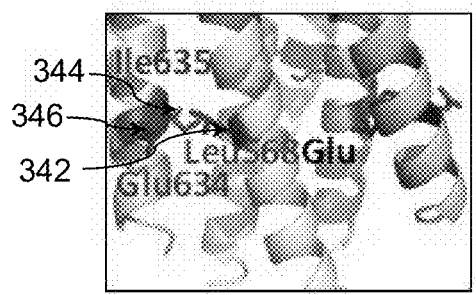
FIG. 3C is a ribbon diagram illustrating the change of the residue Leu568 of HR1 into Glu568.
Figure 3D:
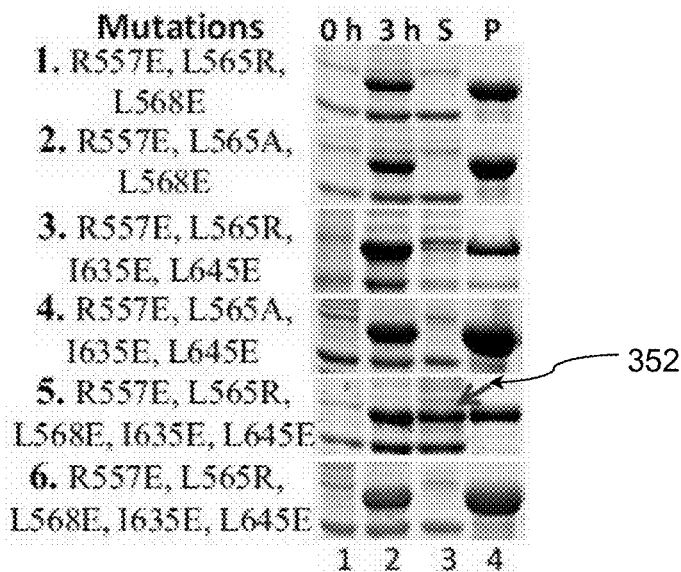
FIG. 3D is an image of SDS-PAGE gels (12%) showing the protein expression and solubility of various gp41 mutants, without IPTG induction (0 h) and 3 hours after IPTG induction (3 h).

Introduction of mutations that disrupt intra-molecular HR1-HR2 interactions should disfavor the formation of hexa-helical bundle and stabilize gp41 in a prehairpin intermediate structure, where the chains would be held by inter-molecular HR1-HR1 interactions and the NITER epitopes would be better exposed (30, 31).

Tags—

Attachment of a trimerization tag such as the phage T4 fold on might help nucleate gp41 folding into a trimer (47). Fusion to Soc (SEQ ID NO: 2), which forms a trimer on T4 capsid, would display gp41 trimers on the phage nanoparticle (42, 48).

Deletion of Immunodominant (ID) Region—

Disclosed embodiments of this present invention show that deletion of part of the apical loop between HR1 and HR2 helices (FIG. 2A; amino acids Q577-T605), will have important consequences for gp41 recombinant design: i) this sequence was reported to consist of ID epitopes (49-51). The amino acids Q577-T605 were deleted in the Soc-gp41ΔID mutant and amino acids L684-V705 were deleted in both the recombinants.

Although strong Ab responses are directed towards this region, these Abs do not neutralize the virus. On the other hand, they might enhance HIV-1 infection through a complement-mediated mechanism (52, 53). Deletion of this region therefore could improve the immunogenicity of gp41 by diverting the Ab responses to the relatively poorly immunogenic NITER epitopes (32). ii) since this sequence consists of two cysteine residues (C598 and C604), their deletion would minimize disulphide crosslinking and insolubilization. iii) deletion of 24 of the 46 amino acids of the loop would favor the tri-helical prehairpin structure rather than the hexa-helical bundle that requires kinking of the intervening loop (FIG. 1B).

According to some disclosed embodiments, two full-length recombinant gp41 proteins were constructed, one with the ID sequence (Soc-gp41, SEQ ID NO: 3) and another without it (Soc-gp41ΔID, SEQ ID NO: 4), containing the fusion peptide, the ectodomain and the cytoplasmic domain, but not the 22-amino acid (Transmembrane domain was found to be toxic; data not shown). Soc-fusions with a 4-amino acid flexible linker (SASA) in between Soc and gp41 were used in these experiments because the constructs are eventually displayed on T4 phage (see below). Both Soc-gp41 and Soc-gp41ΔID recombinant proteins were over-expressed in *E. coli* (~20% of total cell protein) (FIGS. 2B and 2C, lane 3) and as predicted, partitioned into insoluble inclusion bodies (FIGS. 2B and 2C; compare lane 4 of soluble fraction with lane 5 of insoluble fraction). The soluble supernatant (S) and insoluble pellet (P) fractions were analyzed. Std, molecular size standards. However, they exhibited distinct solubilization behavior (FIG. 2D). In FIG. 2D, the insoluble inclusion bodies (IB) were treated with various denaturing reagents and centrifuged at 12,000 g for 10 min. The supernatants (S) and pellets (P) were analyzed by SDS-PAGE. Soc-gp41 could not be solubilized either with 8 M urea or 6 M GnHCl (FIG. 2D, upper panel, lanes 4 and 6), whereas Soc-gp41ΔID was nearly completely solubilized under the same conditions (FIG. 2D, lower panel, lanes 4 and 6) and could be purified to near homogeneity by HisTrap affinity chromatography (FIG. 2E). Curve 212 represents absorbance units and curve 214, the imidazole gradient. Inset shows SDS-PAGE (12%) image of the purified protein.

Furthermore, the concentration of urea could be reduced to 2 M and the protein remained in solution. However, precipitation occurred when the urea concentration was further reduced. On the other hand, the Soc-gp41 protein required SDS, a strong ionic detergent, for solubilization. Even with SDS, only partial solubilization was achieved (FIG. 2D, upper panel, lane 2), and SDS was required throughout purification to maintain solubility.

Mutations in HR1 and HR2 Helices—

A series of interactions between HR1 and HR2 helices are central to the assembly of a trimeric envelope structure and these interactions dynamically change during membrane fusion and virus entry (18, 33, 54) (FIGS. 1B and 3A). These include inter-molecular interactions between the HR1 helices leading to trimerization, and intra-molecular interactions by the looping back of HR2 helices into the hydrophobic grooves between two HR1 helices (FIGS. 1B and 3A) (33). We hypothesized that destabilization of the intra-molecular interactions would reduce nonspecific aggregation, but importantly, it would favor the tri-helical prehairpin structure, not the hexa-helical bundle because a combination of shortened apical loop and mutations would make it energetically unfavorable.

From the crystal structure of gp41 hexa-helical bundle (FIG. 3A) (33), interactions that, if mutated would weaken the HR1-HR2 interactions but not the HR1-HR1 interactions, have been identified. For instance, mutation of Arg557 (332) to Glu would change the electrostatic attraction between Arg557 (332) and Glu648 (334) to electrostatic repulsion (FIG. 3B), and introduction of Glu at Leu568 (342) would disrupt the hydrophobic interactions between Leu568 (342) and Ile635 (344) and at the same time create electrostatic repulsion with Glu634 (346) (FIG. 3C). Using these principles, six mutant clones were constructed in the background of Soc-gp41 MD and their solubility was compared (FIG. 3D). In FIG. 3D, lanes 3 and 4 represent soluble supernatant (s) and insoluble pellet (P) fractions after the cells were lysed with B-PER reagent followed by centrifugation at 12,000 g. All the mutants over-expressed gp41 but the Mutant 5 (SEQ ID NO: 5)—R557E, L565R, L568E, 1635E, L645E—gave the best results, expressing the protein in soluble form (about 40% soluble; lane 3, marked with red arrow 352). Hence this construct, according to some embodiments, namely Soc-gp41 mutant (Soc-gp41M, SEQ ID NO: 5), was selected for further design.

Figures 3E, 3F:
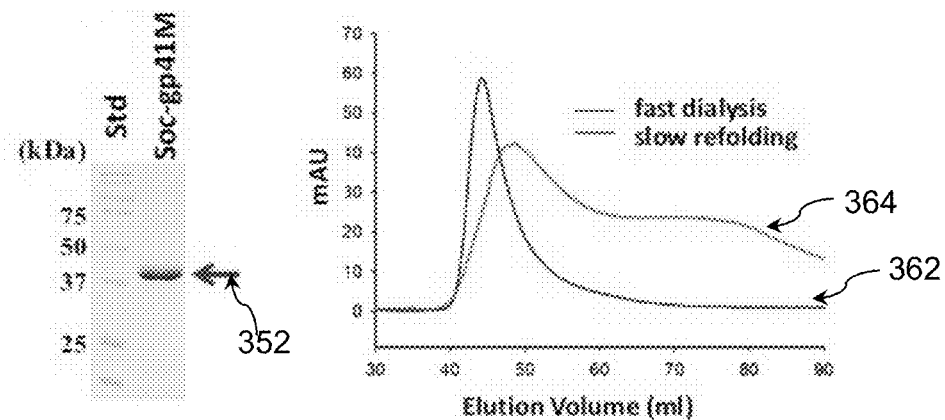
FIG. 3E is an image of an SDS-PAGE gel (12%) showing the purified Soc-gp41M protein.
FIG. 3F is an elution profile of Soc-gp41M by Superdex 200 gel filtration.
Figure 3G:
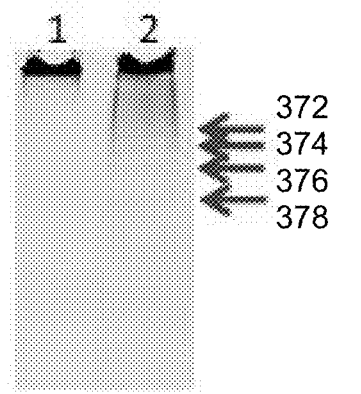
FIG. 3G is an image of a native PAGE (4-20% gradient) of purified Soc-gp41M protein renatured by fast dialysis (lane 1) or by slow refolding (lane 2).

Attempts to purify Soc-gp41M protein from cell lysate, however, were not successful as it did not bind to HisTrap column probably because the protein was misfolded and the histidine tag was buried in the structure. On the other hand, the 8 M urea solubilized protein bound to the column efficiently and could be purified to >95% purity (FIG. 3E). According to some embodiments, the Soc-gp41M protein was purified from inclusion bodies by 8 M urea denaturation followed by HisTrap column chromatography. Purified protein 352 n 8 M urea was then dialyzed against PBS buffer ("fast" dialysis). Std is molecular size standards. The protein remained soluble upon "fast" dialysis against PBS (one-step transition from 8 M urea to PBS), but the resultant protein behaved as a very high mol. wt. species by size exclusion gel filtration chromatography (FIG. 3F, curve 362) Curve 362 represents Soc-gp41M protein renatured by fast dialysis and curve 364 represents the protein renatured by slow refolding. Also, it migrated as a smear by native PAGE (FIG. 3G, lane 1) suggesting that the mutant protein, even though soluble, formed hetero-disperse aggregates (indicated by arrows 372, 374, 376, 378) but not defined oligomers. Native PAGE (4-20% gradient) of purified Soc-gp41M protein renatured by fast dialysis (lane 1) or by slow refolding (lane 2).

Slow Refolding—

It has been hypothesized that the folding kinetics of the extremely hydrophobic gp41 must be controlled in order to channel the process towards the correct folding and oligomerization pathway. A number of variables including protein concentration, pH, reducing agents, L-arginine, and "slow" dialysis were optimized to control folding kinetics, using native PAGE as an assay [L-arginine suppresses protein aggregation and enhances refolding (55)]. Misfolded and aggregated protein would not enter the native gel or migrate as a smear, whereas the folded species would show distinct bands.

Data from a large series of experiments showed that slow dialysis against Tris-HCl buffer, pH 8.0-9.0, protein concentration between 0.25 to 1 mg/ml, 5 mM DTT, and 200 mM L-arginine gave the best results. The gel filtration elution profile of the refolded gp41 under these conditions showed a shift from large aggregates (void volume; FIG. 3F, curve 362) to oligomers (FIG. 3F, curve 364). Native gel electrophoresis showed that a portion of gp41 folded into defined oligomers as evident by the appearance of a ladder of bands (FIG. 3G, lane 2, indicated by arrows 372, 374, 376, 378). However, most of Soc-gp41M still remained as soluble aggregates and stayed near the well (see FIG. 3G, lane 2).

Trimerization Using Foldon Tag—

Figure 4A:
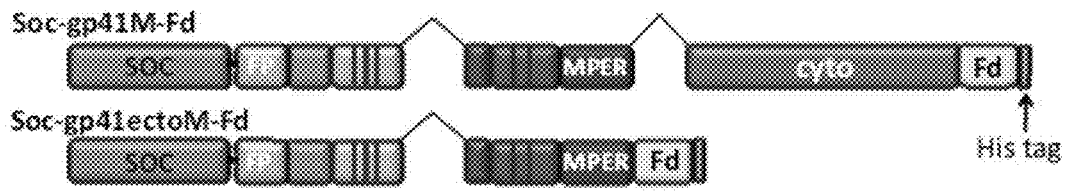
FIG. 4A is a schematic representation of Soc-gp41M-Fd and Soc-gp41ectoM-Fd recombinants.
Figure 4B:
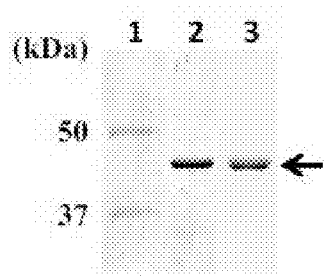
FIG. 4B is an image of an SDS-PAGE gel (12%) of purified Soc-gp41M-Fd protein.
Figure 4C:
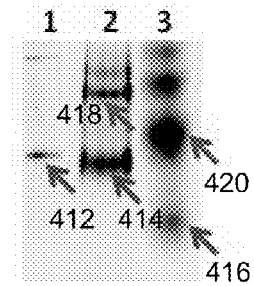
FIG. 4C is an image of a native PAGE (4-20% gradient) of purified Soc-gp41M-Fd and Soc-gp41ectoM-Fd proteins.

Foldon, a 27-amino acid trimerization domain of T4 fibritin, has been extensively used to trimerize foreign domains and proteins (31, 47). We hypothesized that attaching the foldon sequence to gp41 might nucleate trimerization of gp41 at the initial step of the folding pathway. According to some embodiments, we constructed Soc-gp41M-Fd (SEQ ID NO: 6) as well as Soc-gp41ectoM-Fd (SEQ ID NO: 7) in which the cytoplasmic domain was deleted (FIG. 4A). Both the proteins were over-expressed and purified. The results showed that foldon, as predicted, dramatically altered the folding and oligomeric states of gp41, producing trimers and higher order oligomers, and the solubility was also further improved. The Soc-gp41M-Fd protein purified from either the soluble fraction (~500 µg/L culture, FIG. 4B, lane 2), or the insoluble fraction (~20 mg/L culture, FIG. 4B, lane 3) behaved similarly, producing trimers and defined oligomers (FIG. 4C, lanes 1 and 2). In FIG. 4B, lane 1, molecular size standards; lane 2, protein purified from the supernatant of cell lysate; lane 3, protein purified from the inclusion bodies by urea denaturation and slow refolding. In FIG. 4C, lane 1, Soc-gp41M-Fd purified from supernatant; lane 2, Soc-gp41M-Fd purified from inclusion bodies; lane 3, Soc-gp41ectoM-Fd purified from inclusion bodies. Trimer bands are marked with arrows 412, 414, 416; hexamer bands are marked with arrows 418, 420.

Figure 4D:
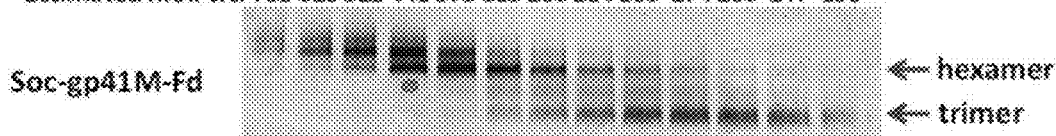
FIG. 4D is an image of a native gel (4-20% gradient) showing the oligomeric state of Soc-gp41M-Fd fractions following Superdex 200 gel filtration.
Figure 4E:
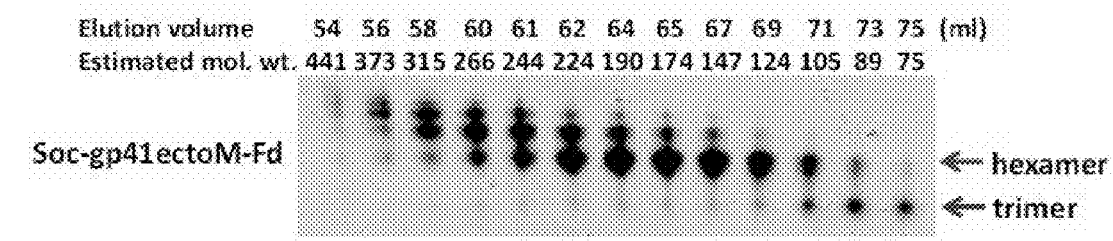
FIG. 4E is an image of a native gel (4-20% gradient) showing the oligomeric state of Soc-gp41ectoM-Fd fractions following Superdex 200 gel filtration.

That the lowermost band in the ladder is a trimer was determined by the elution volume (FIG. 4D) of this species in comparison with the elution volumes of a series of known standard proteins used to calibrate the gel filtration column. The next higher oligomer band in the ladder was determined to be a hexamer. Indeed, unlike the Soc-gp41M which produced mostly aggregates, essentially all the foldon-attached Soc-gp41M-Fd and Soc-gp41ectoM-Fd proteins were recovered as trimers and oligomers (FIG. 4C, lanes 1-3). The gp41 trimers and oligomers could be separated on a size exclusion column (FIGS. 4D and 4E). In FIGS. 4D and 4E, the elution volumes and estimated molecular weight of the fractions are labeled at the top of the lanes. The positions of trimer and hexamer are indicated with arrows.

Indeed, fractions containing mostly trimers could be purified by this method. The distribution of the oligomers did not, however, change by a second round gel filtration of trimer fractions suggesting that the gp41 subunit interactions are of high avidity and not in a dynamic equilibrium. Disclosed embodiments speculate that the basic gp41 oligomer unit is a trimer. Hexamers (and higher order oligomers) are most likely dimers (or multimers) of trimers formed by (nonspecific) interactions between gp41 trimers. Although both Soc-gp41M-Fd and Soc-gp41ectoM-Fd gave similar oligomerization patterns (FIGS. 4D and 4E), we found that a greater fraction of the full-length gp41 oligomerized into trimers than that of the ectodomain construct (FIG. 4C, compare lane 2 (Soc-gp41M-Fd) and 3 (Soc-gp41ectoM-Fd); compare FIGS. 4D (Soc-gp41M-Fd) and 4E (Soc-gp41ectoM-Fd)], suggesting that the bulky cytodomain might have stabilized trimers, probably by restricting trimer-trimer interactions.

gp41 Trimers have a Prehairpin Structure—

Figure 5A:
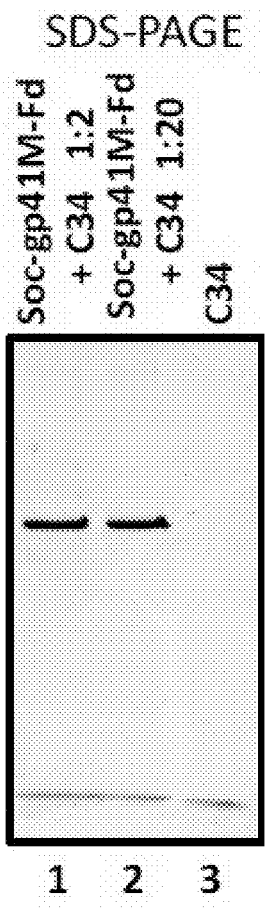
FIG. 5A is an image of an SDS-PAGE gel (12%) showing the HR2 peptide C34 bound to Soc-gp41M-Fd.

For the reasons described above, the gp41M-Fd mutants are predicted to be stabilized in a prehairpin structure. If so, an externally added HR2 peptide should bind to the exposed groove between HR1 helices through inter-molecular interactions (16, 33). To test this hypothesis, a 34-amino acid HR2 peptide (C34, 4 kDa) was added to Soc-gp41M-Fd and the unbound peptide was removed by extensive dialysis using a 10 kDa cut-off membrane. If gp41 trimer is in prehairpin state, it would capture the C34 peptide and form a gp41-C34 complex. The results demonstrated that the C34 peptide was retained with gp41 (FIG. 5A, lane 1). The C34 peptide was added to Soc-gp41M-Fd at a molar ratio of 2 or 20 times C34 to gp41 molecules and gp41 was refolded. The unbound peptide was removed by extensive dialysis using a 10 kDa cut-off membrane. Lane 3, 0.4 µg of C34 peptide used as size standard.

Figure 5B:
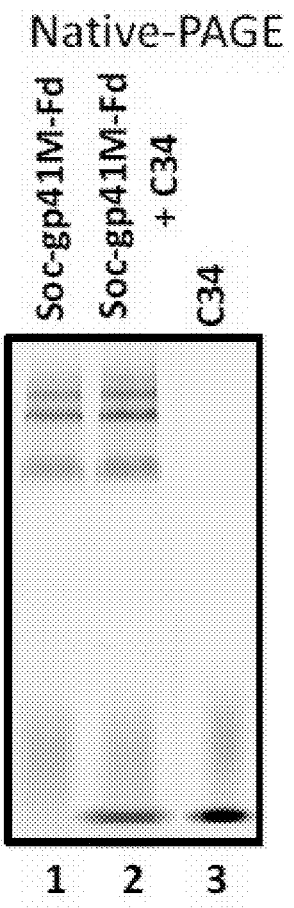
FIG. 5B is an image of a native PAGE gel (4-20% gradient) showing the oligomeric state of Soc-gp41M-Fd with or without the addition of C34 peptide (1:20 molar ratio of Soc-gp41M-Fd to C34).

In fact, the ratio of gp41 to C34 in the complex remained the same whether the molar amount of C34 used was 2-times that of gp41 (FIG. 5A, lane 1) or 20-times that of gp41 (FIG. 5A, lane 2). On the other hand, addition of a 36-amino acid HR1 (N36) peptide resulted in the precipitation of gp41 probably due to uncontrolled HR1-HR1 interactions. Secondly, the folding pattern of gp41 was unaffected by C34 (FIG. 5B, compare lane 1 without C34 to lane 2 with C34), which means that the conformation of gp41 with and without C34 binding was the same. Since C34 binding to HR1 is expected to occur only in the prehairpin conformation, it can be inferred that gp41 folded into the same conformation even in the absence of C34. The samples were electrophoresed prior to removing excess C34 by dialysis. Lane 3, 3 µg of C34 peptide used as size standard.

Neutralizing MPER Epitopes are Well-Exposed in gp41 Trimers—

Figure 6A:
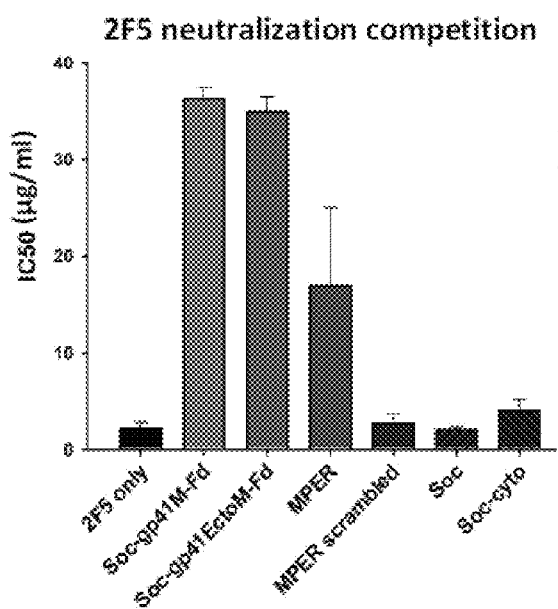
FIG. 6A is a bar graph showing virus neutralization with serial dilutions of purified 2F5 IgG as determined by the TZM/bl assay.
Figure 6B:
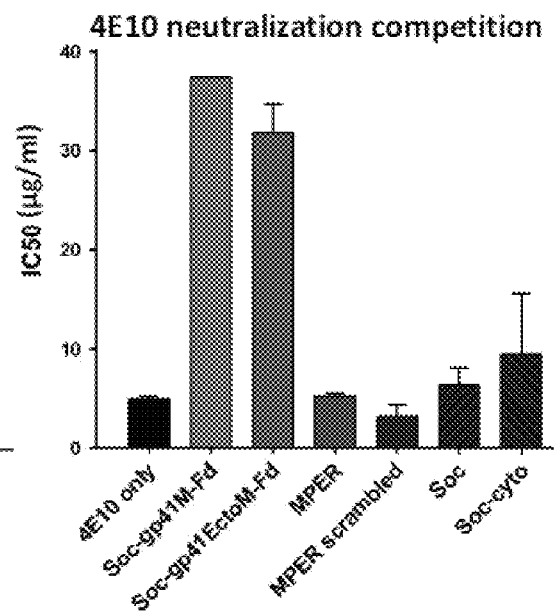
FIG. 6B is a bar graph showing virus neutralization with serial dilutions of purified 4E10 IgG as determined by the TZM/bl assay.

The bnAbs 2F5 and 4E10 bind to the conserved MPER epitopes of gp41 and block HIV-1 entry, presumably by arresting fusion at the prehairpin stage where the epitopes would be well-exposed (31, 34, 35) (see FIG. 1B). Consistent with this hypothesis, these mAbs have the highest affinity to the prehairpin gp41 intermediate, but not to the hexa-helical hairpin bundle (30, 56). If the trimeric Soc-gp41M-Fd and Soc-gp41ectoM-Fd have a prehairpin structure, they should bind to 2F5 and 4E10 mAbs at high affinity and inhibit their ability to neutralize HIV-1 infection. To test this hypothesis, Soc-gp41M-Fd and Soc-gp41ectoM-Fd were added to the TZM/bl pseudovirus neutralization reaction mixture at varying molar ratios of gp41 to mAb, and the amounts of Abs for 50% virus neutralization inhibition (IC50) were determined. The data demonstrated that both the constructs potently inhibited virus neutralization (FIGS. 6A and 6B). gp41 concentration as low as 120 nM was sufficient to compete with the virus for binding to 2F5 and 4E10, causing a 7 to 10-fold raise in the IC50 values (FIGS. 6A and 6B). At a 1:1 molar ratio of gp41 to mAb, 45-76% inhibition of virus neutralization was observed. The full-length gp41 showed slightly higher inhibition than the ectodomain construct. No significant difference was observed whether gp41 was preincubated with the mAb or added directly to the neutralization mixture. Validating these results, the 23-amino acid MPER linear peptide, but not the scrambled MPER peptide, inhibited 2F5 neutralization (FIGS. 6A and 6B). Also, the MPER peptide did not affect 4E10 neutralization, consistent with the fact that the 4E10 mAb recognizes a conformational epitope. Neither the gp41 cytoplasmic domain (Soc-cyto) nor Soc controls showed significant inhibition, attesting to the specificity of gp41-2F5/4E10 interactions. These results further support that the trimeric gp41M-Fd constructs are stabilized in a prehairpin structure exposing the MPER neutralization epitopes in a functionally relevant conformation.

In FIGS. 6A and 6B, serial dilutions of purified 2F5 (FIG. 6A) or 4E10 (FIG. 6B) IgG were added to 96-well plates. gp41 trimers or other control competitors were added to the mAb and incubated for 30 min at 37° C. SF162 virus was added to the plate and incubated for 30 min at 37° C., followed by the addition of TZM/bl cells. After incubation for 48 h at 37° C., the cells were lysed, and concentration of half-maximal inhibition (IC50) was calculated from the luciferase activities determined by luminescence measurements. The sequence of MPER peptide is LELDK-WASLWNWFNITNWLWYIK (amide) and that of MPER scrambled peptide is LSINEAFKWLDWWTLNDL-WYIWK (amide). Soc-cyto is the fusion of cytoplasmic domain of gp41 to the C-terminus of Soc. The protein was over-expressed and purified from E. coli after 8 M urea denaturation followed by refolding.

Display of gp41 Trimers on the Bacteriophage T4 Nanoparticle—

Figures 7E, 7F:
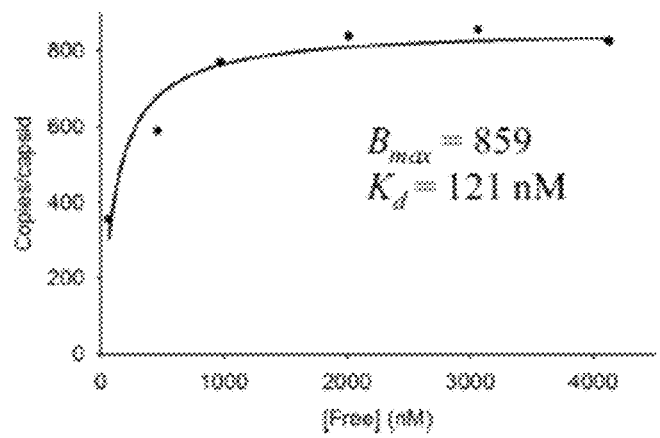
FIG. 7E is the saturation binding curve of Soc-gp41M-Fd.
FIG. 7F is a table showing the binding parameters of Soc and Soc-gp41 fusion recombinants.

Eight hundred and seventy copies of a small outer capsid protein, Soc (9 kDa), decorate the surface of T4 capsid. Soc is a monomer in solution but trimerizes upon binding to capsid at the quasi-3-fold axes (FIG. 7A) (42). Each Soc molecule binds to two gp23* major capsid protein subunits clamping adjacent capsomers and reinforcing the capsid structure. Both the C- and N-termini are exposed on the capsid surface, with the C-termini at the quais-3-fold axes and the N-termini at the quasi-2-fold axes (FIG. 7A). Disclosed embodiments hypothesized that by fusing gp41 to the C-terminus of Soc and displaying it on T4, the trimeric gp41 would be stably displayed at the 3-fold axes of the phage capsid. Such particles with arrays of gp41 trimers would allow structure-function studies as well as enhance immunogenicity (64). The gp41 trimers assembled on hoc⁻soc⁻ capsids nearly as efficiently as native Soc (FIGS. 7B, 7C, 7D, 7E and 7F). Soc-gp41M-Fd binding increased with increasing ratios of Soc-gp41 molecules to capsid binding sites, reaching saturation at a ratio of ~20:1 (FIG. 7B). In FIG. 7B, about $2 \times 10^{10}$ hoc⁻soc⁻ phage particles were incubated with increasing ratios of Soc-gp41M-Fd molecules to capsid binding sites (1:1 to 40:1, labeled at the top) and assembly was carried out. Lanes: 1, control hoc⁻soc⁻ phage; 2, 4, 6, 8, 10 and 12, phage displaying the bound fusion protein Soc-gp41M-Fd (B); 3, 5, 7, 9, 11 and 13, unbound protein in the supernatant (U). The position of the major capsid protein gp23* is marked with arrow 712.

In FIG. 7C, the bound Soc-gp41ectoM-Fd protein was indicated with a red arrow 714 (lane 2). In FIG. 7D, the 49 kDa CPP-Soc-gp41M-Fd protein migrates to the same position as the 48.7 kDa gp23* (indicated with red arrow 716).

The apparent association constant ($K_d$) calculated from the saturation binding curve (FIG. 7E) was 121 nM and the maximum copy number of bound gp41 ($B_{max}$) was about 859 per capsid, which is close to the copy number of 870 when all the Soc binding sites are occupied. Similar binding behavior as well as $K_d$ and $B_{max}$ values was observed for Soc-gp41ectoM-Fd (FIGS. 7C and 7F). In FIG. 7E, the density volumes of bound and unbound proteins from SDS-PAGE (12%) were determined by laser densitometry and normalized to that of gp23* present in the respective lane. The copy numbers were determined in reference to gp23* (930 copies per capsid). The data were plotted as one site saturation ligand binding curve and fitted by non-linear regression using the SigmaPlot10.0 software and the calculated binding parameters are shown. $K_d$, apparent binding constant; $B_{max}$, maximum copy number per phage particle. The binding parameters of Soc and Soc-gp41 fusion recombinants are shown in FIG. 7F. Since the CPP-Soc-gp41M-Fd band overlapped with the gp23* band, gp23* density was subtracted and the copy number was determined in reference to the tail sheath protein, gp18 (138 copies per phage; marked with arrow 716 in FIG. 7D, lane 2).

According to some disclosed embodiments, to further improve the gp41 nanoparticle design, a 13-amino acid cell penetration peptide (CPP (SEQ ID NO: 8), CPP-Tat (PGRK- KRRQRRPPQ), was attached to the N-terminus of Soc-gp41. CPPs are 10-30 amino acid peptides rich in basic amino acids that facilitate passage of attached cargo molecules across the cell membrane (57). The CPP-Tat derived from HIV-1 trans-activator protein, TAT, is one of the most efficient CPPs (57). CPP-Soc-gp41M-Fd (SEQ ID NO: 9) could be over-expressed, purified, and bound to T4 capsid efficiently, and the binding parameters are also similar (FIGS. 7D and 7F). Thus, CPP or another molecule such as the CD40 Ligand (58) can be oriented at the quasi-2-fold axes for targeting of the nanoparticle to antigen presenting cells such as the dendritic cells. Our recent experiments show that T4 particles displaying targeting molecules attached to Soc are taken up by cells at high efficiency (unpublished results).

Although the key interactions between HIV-1 and host cell have been well established, the extraordinary genetic diversity of viral envelope and masking of essential epitopes by glycosylation made it difficult to design recombinants that can induce protective immune responses (59, 60). However, the HIV-1 virus, like many type-1 fusion viruses, undergoes dynamic transitions during entry, exposing some of the vulnerable sites on the cell surface making them accessible to therapeutics and neutralizing Abs. The prehairpin intermediate is one such target because it is relatively stable with a half-life on the order of several minutes (19), and its ectodomain most extended and the conserved neutralization epitopes most exposed (FIG. 1B) (30, 31, 59, 60). Indeed, Enfuvirtide, a potent 20-amino acid entry inhibitor approved for clinical use (61), and a series of bnAbs, such as 2F5 and 4E10, arrest virus entry by binding to this intermediate. Design of gp41 recombinants stabilized in a prehairpin structure, therefore, will have important implications for understanding the mechanism as well as for development of effective therapeutics and vaccines.

The extremely hydrophobic gp41 is notoriously prone to aggregation and attempts to produce soluble gp41 have not been successful (36). Previous studies could only produce short truncated parts of the gp41 ectodomain, most containing only the HR1 and HR2 helices (31, 38, 39, 62). These and other synthetic peptide mimics could not elicit potent bnAbs, leading to the hypothesis that other gp41 structural and functional motifs might be essential to mimic the true prehairpin conformation (see FIG. 1B) (40, 41). These might include, in addition to HR1/HR2 helices and MPER, the fusion peptide at the N-terminus and the cytoplasmic domain at the C-terminus, but none of the gp41 recombinants produced so far include these highly hydrophobic regions.

Figure 1C:
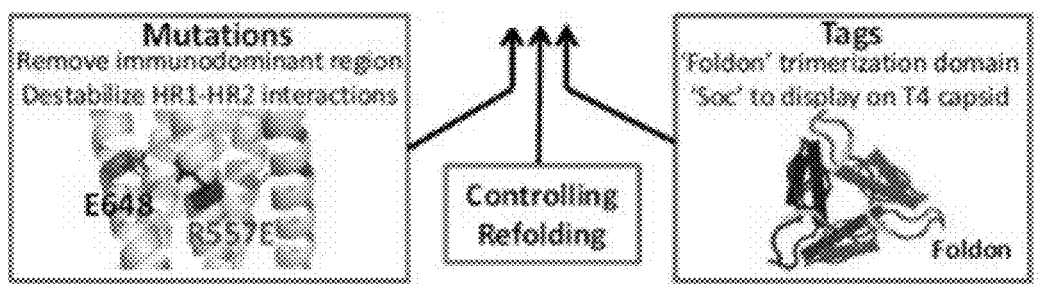
FIG. 1C is a schematic diagram illustrating strategies to generate gp41 recombinant trimers in prehairpin structure.
Figure 2A:
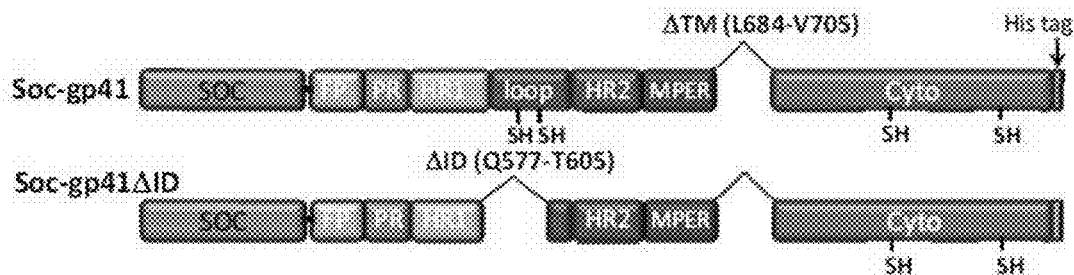
FIG. 2A is a schematic representation of Soc-gp41 and Soc-gp41ΔID recombinants.
Figure 2B:
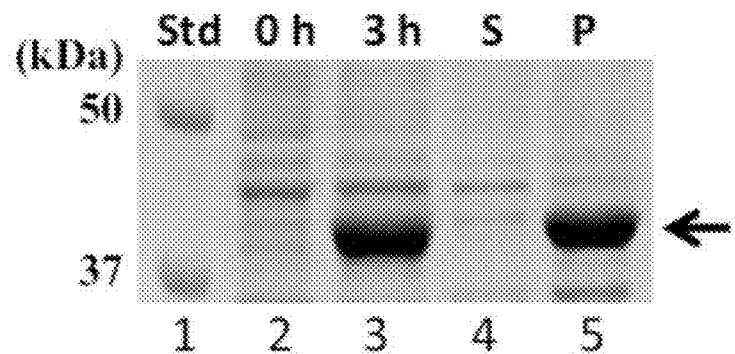
FIG. 2B is an image of an SDS-PAGE gel showing the protein patterns of Soc-gp41 without IPTG induction (0 h) or 3 hours after IPTG induction (3 h).
Figure 2C:
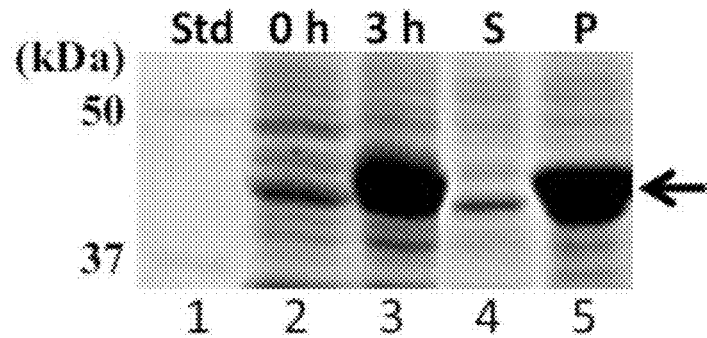
FIG. 2C is an image of an SDS-PAGE gel showing the protein patterns of Soc-gp41ΔID without IPTG induction (0 h) or 3 hours after IPTG induction (3 h).
Figure 2D:
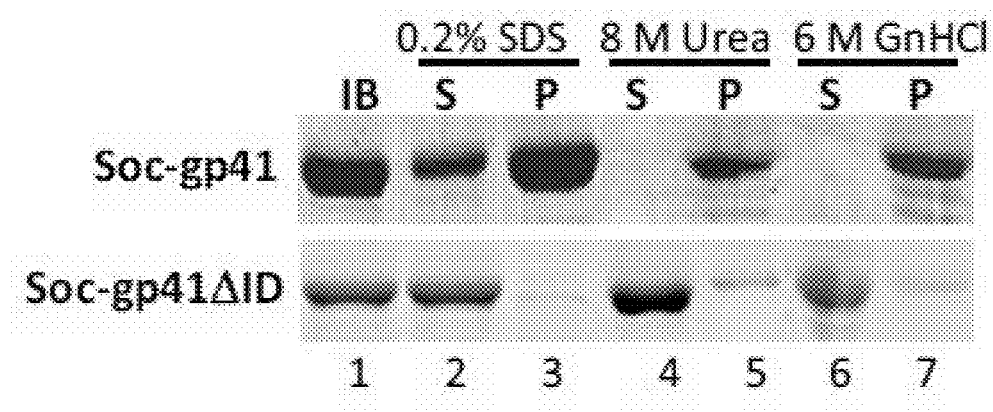
FIG. 2D is an image of SDS-PAGE gels comparing the solubility of Soc-gp41 (upper panel) with Soc-gp41_ID (lower panel).
Figure 2E:
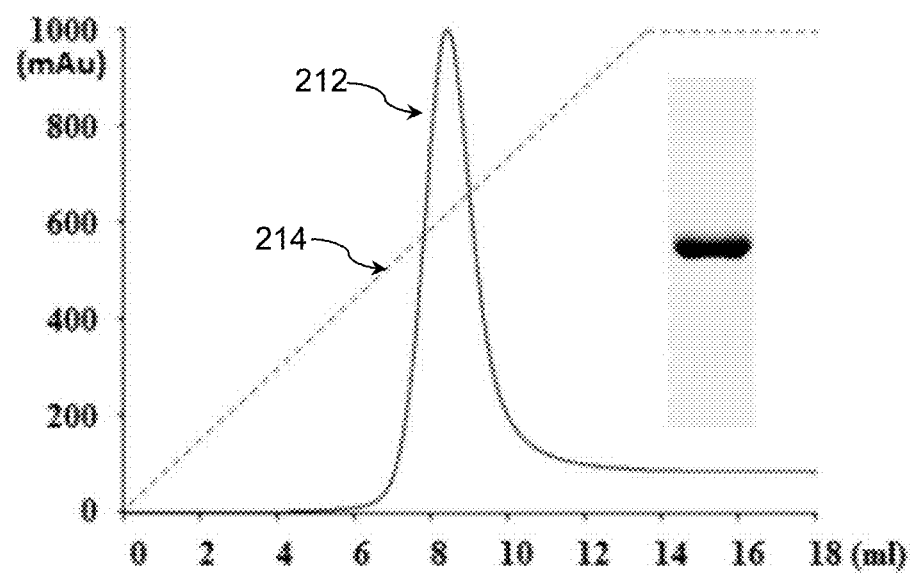
FIG. 2E is an elution profile of Socgp41ΔID on a HisTrap column.
Figure 8:
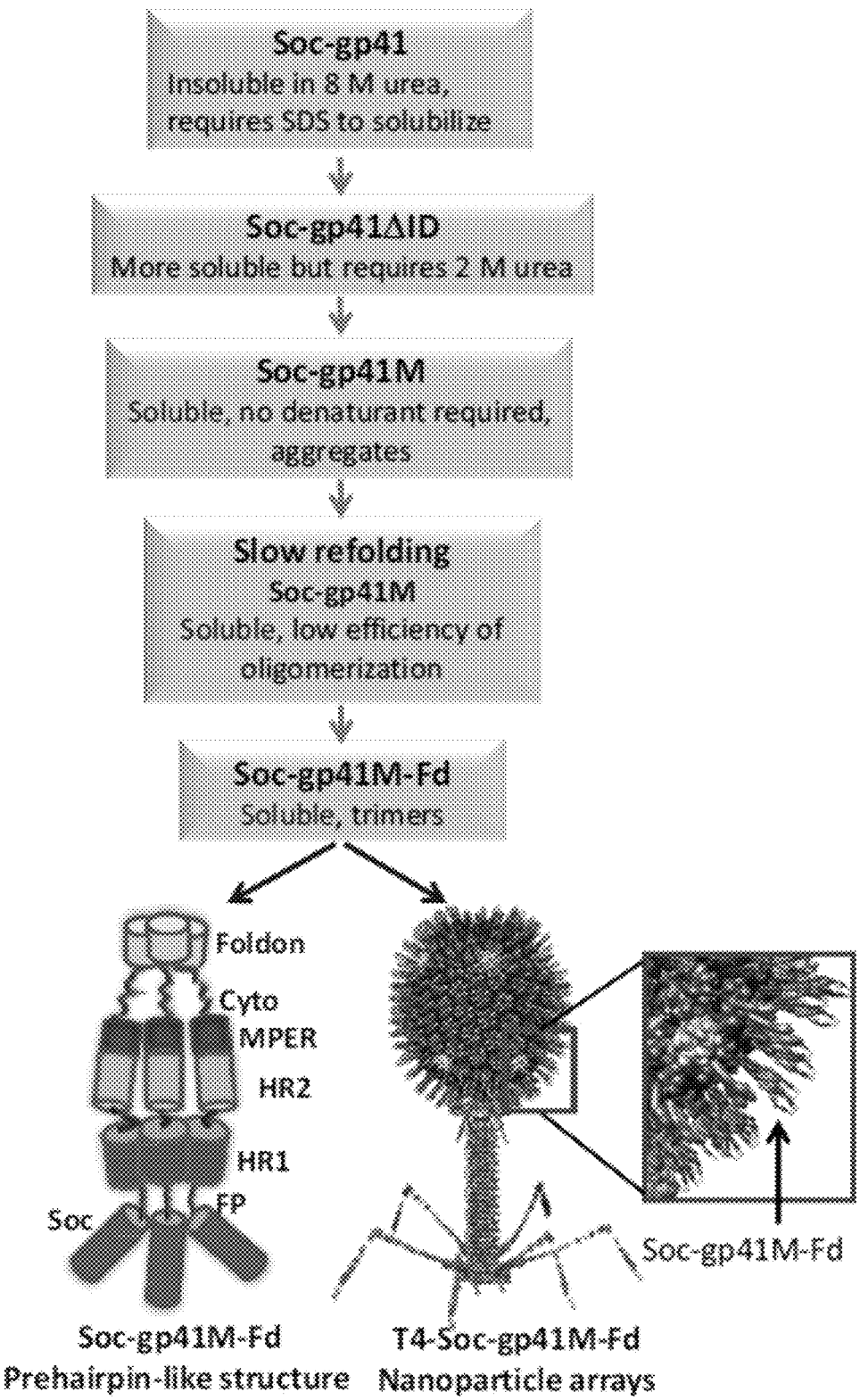
FIG. 8 is a flow chart showing a series of approaches to generate soluble as well as phage T4 nanoparticle arrayed gp41 trimers with schematic diagrams of soluble and displayed trimers are shown at the bottom.

Disclosed embodiments hypothesized that three key problems should be addressed in order to generate a soluble trimeric gp41 stabilized in a prehairpin structure (FIG. 1C). First, the inter-molecular interactions between HR1 and HR2 helices that lead to hexa-helical bundle formation as well as nonspecific aggregation should be disrupted to stabilize the molecule in a three-stranded coil. This we achieved by deleting part of the apical loop and the five C-terminal amino acids of HR1 helix, as well as converting some of the complementary charge-charge and hydrophobic interactions into electrostatic repulsion, leaving intact the MPER epitope residues. These modifications greatly enhanced the solubility of gp41, however only a small fraction of the protein oligomerized into trimers (FIG. 8). Attachment of a foldon tag that has strong propensity to trimerize was necessary to trimerize gp41. Presumably, the foldon helped nucleate gp41 folding and assembly into a trimer. Since the tag is present at the C-terminal end, trimerization was probably initiated at this end and propagated through the rest of the molecule leading to folding of the protein into a three-stranded coiled coil through the strong HR1-HR1 interactions. Kinetically slowing down this process at relatively low protein concentration was also necessary, otherwise nonspecific inter-chain interactions presumably channeled the protein into abortive folding pathways leading to rapid and uncontrolled aggregation.

Although disclosed embodiments yielded predicted outcomes (FIG. 8), each approach by itself was insufficient to produce gp41 trimers. For instance, introduction of mutations greatly improved solubility but the protein chains still coalesced into aggregates because folding was not trimer-directed. Both trimerization tag attachment and slow refolding were necessary to correct this problem. Although hexamers and higher order oligomers were produced in addition to trimers, the core structure of all the oligomers appears to be a trimer and the higher order oligomers are probably multimers of trimers formed by nonspecific interactions between trimers. This is not unexpected because several hydrophobic patches would be exposed in the gp41 ectodomain, which would otherwise be stabilized by interactions with the gp120 domains in the native spike. These would lead to multimerization of trimers, a commonly observed phenomenon even with the gp140 trimers produced by heterologous expression systems where only short regions of the gp41 ectodomain are exposed.

Evidence indicates that the gp41 trimers have a structure mimicking the prehairpin intermediate in which the external grooves of the three-stranded HR1 helices were not occupied by HR2 helices. Consistent with this prediction, a 34-amino acid HR2 peptide efficiently bound to the gp41 trimers and the oligomerization pattern was identical with or without the peptide. Had the trimers been in a hexa-helical bundle conformation, the HR2 peptide would not have bound to gp41 and the oligomerization patterns would have been different (16, 33). The prehairpin intermediate conformation of gp41 trimers was further supported by virus neutralization assays. The gp41 trimers potently inhibited 2F5 or 4E10 virus neutralization even at an equimolar ratio of gp41 to mAb and in the presence of excess virus, consistent with previous evidence that the MPER epitopes exposed in the prehairpin intermediate bind to 2F5 and 4E10 at the highest affinity (30, 31).

The potential use of gp41 trimer as an immunogen can be further enhanced by linking the recombinants to a robust platform that can induce strong immune responses. The bacteriophage T4 display provides a simple yet powerful strategy to convert soluble antigens into nano-particulate antigens by attaching Soc to one end of the antigen (63, 64). We have previously shown that such nanoparticles displaying HIV-1 Gag p24 and other antigens induced strong Ab as well as cellular responses (64, 65). Attachment of Soc to the N-terminus did not interfere with the folding or trimerization of gp41, neither did it affect binding to T4 capsid. Indeed, the Soc-binding sites were essentially saturated, resulting in the decoration of T4 phage with ~290 trimers of gp41. Since Soc C-termini are projected outward at the quasi-3-fold axes (FIG. 7A) (42), the C-terminally attached gp41 trimers would be extending away from the capsid surface (FIG. 8), thereby exposing the MPER epitopes for capture by antigen presenting cells. Furthermore, additional targeting ligands, such as CPP, can be incorporated, potentially enhancing the broad applicability of these high density nanoparticle arrayed gp41.

In conclusion, using molecular genetics and biochemical approaches a series of hypotheses were tested (FIG. 8), leading to the generation of soluble full-length gp41 trimers containing the fusion peptide, the ectodomain, and the cytoplasmic domain, as well as the same arrayed on phage nanoparticles. The trimers are stabilized in a prehairpin-like structure in which the HR1 helical grooves and MPER epitopes would be well exposed.

These, for the first time, allow structure determination of this critical intermediate, screening for novel therapeutics, development of new diagnostics, and design of gp41-based HIV-1 vaccines. The recent RV144 trial showed a correlation between protection against HIV-1 infection and generation of Abs to the gp120 variable loop V2 (6, 66). The full-length gp41 antigens generated in our study can be used in conjunction with gp120 to further improve the immunogenicity of the vaccine to induce binding and neutralizing Abs as well as cellular responses. With this in mind, we are using similar approaches to prepare other HIV-1 envelope immunogens such as gp140 trimers and V1/V2 loops to test their potential as effective HIV-1 vaccines.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

REFERENCES

The following references are referred to above and/or describe technology that may be used with the present invention and contents and disclosures of the following references are incorporated herein by reference:

1. Maltez, F., Doroana, M., Branco, T., and Valente, C. (2011) Recent advances in antiretroviral treatment and prevention in HIV-infected patients. *Curr Opin HIV AIDS* 6 Suppl 1, S21-30
2. Meadows, D. C., and Gervay-Hague, J. (2006) Current developments in HIV chemotherapy. *Chem Med Chem* 1, 16-29
3. Walker, L. M., Huber, M., Doores, K. J., Falkowska, E., Pejchal, R., Julien, J. P., Wang, S. K., Ramos, A., Chan-Hui, P. Y., Moyle, M., Mitcham, J. L., Hammond, P. W., Olsen, O. A., Phung, P., Fling, S., Wong, C. H., Phogat, S., Wrin, T., Simek, M. D., Koff, W. C., Wilson, I. A., Burton, D. R., and Poignard, P. (2011) Broad neutralization coverage of HIV by multiple highly potent antibodies. *Nature* 477, 466-470
4. Kwong, P. D., Mascola, J. R., and Nabel, G. J. (2012) Rational Design of Vaccines to Elicit Broadly Neutralizing Antibodies to HIV-1. *Cold Spring Harbor Perspectives in Biology* 4
5. McElrath, M. J., and Haynes, B. F. (2010) Induction of immunity to human immunodeficiency virus type-1 by vaccination. *Immunity* 33, 542-554
6. Rerks-Ngarm, S., Pitisuttithum, P., Nitayaphan, S., Kaewkungwal, J., Chiu, J., Paris, R., Premsri, N., Namwat, C., de Souza, M., Adams, E., Benenson, M., Gurunathan, S., Tartaglia, J., McNeil, J. G., Francis, D. P., Stablein, D., Birx, D. L., Chunsuttiwat, S., Khamboonruang, C., Thongcharoen, P., Robb, M. L., Michael, N. L., Kunasol, P., and Kim, J. H. (2009) Vaccination with ALVAC and AIDSVAX to prevent HIV-1 infection in Thailand. *N Engl J Med* 361, 2209-2220
7. Burton, D. R., Poignard, P., Stanfield, R. L., and Wilson, I. A. (2012) Broadly neutralizing antibodies present new prospects to counter highly antigenically diverse viruses. *Science* 337, 183-186
8. Boutwell, C. L., Rolland, M. M., Herbeck, J. T., Mullins, J. I., and Allen, T. M. (2010) Viral evolution and escape during acute HIV-1 infection. *J Infect Dis* 202 Suppl 2, S309-314
9. Pejchal, R., and Wilson, I. A. (2010) Structure-based vaccine design in HIV: blind men and the elephant? *Curr Pharm Des* 16, 3744-3753
10. Wyatt, R., and Sodroski, J. (1998) The HIV-1 envelope glycoproteins: fusogens, antigens, and immunogens. *Science* 280, 1884-1888
11. Arthos, J., Cicala, C., Martinelli, E., Macleod, K., Van Ryk, D., Wei, D., Xiao, Z., Veenstra, T. D., Conrad, T. P., Lempicki, R. A., McLaughlin, S., Pascuccio, M., Gopaul, R., McNally, J., Cruz, C. C., Censoplano, N., Chung, E., Reitano, K. N., Kottilil, S., Goode, D. J., and Fauci, A. S. (2008) HIV-1 envelope protein binds to and signals through integrin alpha4beta7, the gut mucosal homing receptor for peripheral T cells. *Nat Immunol* 9, 301-309
12. Cicala, C., Martinelli, E., McNally, J. P., Goode, D. J., Gopaul, R., Hiatt, J., Jelicic, K., Kottilil, S., Macleod, K., O'Shea, A., Patel, N., Van Ryk, D., Wei, D., Pascuccio, M., Yi, L., McKinnon, L., Izulla, P., Kimani, J., Kaul, R., Fauci, A. S., and Arthos, J. (2009) The integrin alpha4beta7 forms a complex with cell-surface CD4 and defines a T-cell subset that is highly susceptible to infection by HIV-1. *Proc Natl Acad Sci USA* 106, 20877-20882
13. Geijtenbeek, T. B., Krooshoop, D. J., Bleijs, D. A., van Vliet, S. J., van Duijnhoven, G. C., Grabovsky, V., Alon, R., Figdor, C. G., and van Kooyk, Y. (2000) DC-SIGN-ICAM-2 interaction mediates dendritic cell trafficking. *Nat Immunol* 1, 353-357
14. Dalgleish, A. G., Beverley, P. C., Clapham, P. R., Crawford, D. H., Greaves, M. F., and Weiss, R. A. (1984) The CD4 (T4) antigen is an essential component of the receptor for the AIDS retrovirus. *Nature* 312, 763-767
15. Berger, E. A., Murphy, P. M., and Farber, J. M. (1999) Chemokine receptors as HIV-1 coreceptors: roles in viral entry, tropism, and disease. *Annu Rev Immunol* 17, 657-700
16. Furuta, R. A., Wild, C. T., Weng, Y., and Weiss, C. D. (1998) Capture of an early fusion-active conformation of HIV-1 gp41. *Nat Struct Biol* 5, 276-279
17. Colman, P. M., and Lawrence, M. C. (2003) The structural biology of type I viral membrane fusion. *Nat Rev Mol Cell Biol* 4, 309-319
18. Melikyan, G. B., Markosyan, R. M., Hemmati, H., Delmedico, M. K., Lambert, D. M., and Cohen, F. S. (2000) Evidence that the transition of HIV-1 gp41 into a six-helix bundle, not the bundle configuration, induces membrane fusion. *J Cell Biol* 151, 413-423
19. Chan, D. C., and Kim, P. S. (1998) HIV entry and its inhibition. *Cell* 93, 681-684
20. Weissenhorn, W., Dessen, A., Harrison, S. C., Skehel, J. J., and Wiley, D. C. (1997) Atomic structure of the ectodomain from HIV-1 gp41. *Nature* 387, 426-430
21. Walker, L. M., and Burton, D. R. (2010) Rational antibody-based HIV-1 vaccine design: current approaches and future directions. *Curr Opin Immunol* 22, 358-366
22. Phogat, S., and Wyatt, R. (2007) Rational modifications of HIV-1 envelope glycoproteins for immunogen design. *Curr Pharm Des* 13, 213-227
23. Muster, T., Steindl, F., Purtscher, M., Trkola, A., Klima, A., Himmler, G., Ruker, F., and Katinger, H. (1993) A conserved neutralizing epitope on gp41 of human immunodeficiency virus type 1. *J Virol* 67, 6642-6647

24. Zwick, M. B., Labrijn, A. F., Wang, M., Spenlehauer, C., Saphire, E. O., Binley, J. M., Moore, J. P., Stiegler, G., Katinger, H., Burton, D. R., and Parren, P. W. (2001) Broadly neutralizing antibodies targeted to the membrane-proximal external region of human immunodeficiency virus type 1 glycoprotein gp41. *J Virol* 75, 10892-10905

25. Barbato, G., Bianchi, E., Ingallinella, P., Hurni, W. H., Miller, M. D., Ciliberto, G., Cortese, R., Bazzo, R., Shiver, J. W., and Pessi, A. (2003) Structural analysis of the epitope of the anti-HIV antibody 2F5 sheds light into its mechanism of neutralization and HIV fusion. *J Mol Biol* 330, 1101-1115

26. Brunel, F. M., Zwick, M. B., Cardoso, R. M., Nelson, J. D., Wilson, I. A., Burton, D. R., and Dawson, P. E. (2006) Structure-function analysis of the epitope for 4E10, a broadly neutralizing human immunodeficiency virus type 1 antibody. *J Virol* 80, 1680-1687

27. Hessell, A. J., Rakasz, E. G., Tehrani, D. M., Huber, M., Weisgrau, K. L., Landucci, G., Forthal, D. N., Koff, W. C., Poignard, P., Watkins, D. I., and Burton, D. R. (2009) Broadly neutralizing monoclonal antibodies 2F5 and 4E10 directed against the human immunodeficiency virus type 1 gp41 membrane-proximal external region protect against mucosal challenge by simian-human immunodeficiency virus SHIVBa-L. *J Virol* 84, 1302-1313

28. Mascola, J. R., Lewis, M. G., Stiegler, G., Harris, D., VanCott, T. C., Hayes, D., Louder, M. K., Brown, C. R., Sapan, C. V., Frankel, S. S., Lu, Y., Robb, M. L., Katinger, H., and Birx, D. L. (1999) Protection of Macaques against pathogenic simian/human immunodeficiency virus 89.6PD by passive transfer of neutralizing antibodies. *J Virol* 73, 4009-4018

29. Mascola, J. R., Stiegler, G., VanCott, T. C., Katinger, H., Carpenter, C. B., Hanson, C. E., Beary, H., Hayes, D., Frankel, S. S., Birx, D. L., and Lewis, M. G. (2000) Protection of macaques against vaginal transmission of a pathogenic HIV-1/SIV chimeric virus by passive infusion of neutralizing antibodies. *Nat Med* 6, 207-210

30. Frey, G., Chen, J., Rits-Volloch, S., Freeman, M. M., Zolla-Pazner, S., and Chen, B. (2010) Distinct conformational states of HIV-1 gp41 are recognized by neutralizing and non-neutralizing antibodies. *Nat Struct Mol Biol* 17, 1486-1491

31. Frey, G., Peng, H., Rits-Volloch, S., Morelli, M., Cheng, Y., and Chen, B. (2008) A fusion-intermediate state of HIV-1 gp41 targeted by broadly neutralizing antibodies. *Proc Natl Acad Sci USA* 105, 3739-3744

32. Montero, M., van Houten, N. E., Wang, X., and Scott, J. K. (2008) The membrane-proximal external region of the human immunodeficiency virus type 1 envelope: dominant site of antibody neutralization and target for vaccine design. *Microbiol Mol Biol Rev* 72, 54-84, table of contents 33. Chan, D. C., Fass, D., Berger, J. M., and Kim, P. S. (1997) Core structure of gp41 from the HIV envelope glycoprotein. *Cell* 89, 263-273

34. Chakrabarti, B. K., Walker, L. M., Guenaga, J. F., Ghobbeh, A., Poignard, P., Burton, D. R., and Wyatt, R. T. (2011) Direct antibody access to the HIV-1 membrane-proximal external region positively correlates with neutralization sensitivity. *J Virol* 85, 8217-8226

35. de Rosny, E., Vassell, R., Jiang, S., Kunert, R., and Weiss, C. D. (2004) Binding of the 2F5 monoclonal antibody to native and fusion-intermediate forms of human immunodeficiency virus type 1 gp41: implications for fusion-inducing conformational changes. *J Virol* 78, 2627-2631

36. Scholz, C., Schaarschmidt, P., Engel, A. M., Andres, H., Schmitt, U., Faatz, E., Balbach, J., and Schmid, F. X. (2005) Functional solubilization of aggregation-prone HIV envelope proteins by covalent fusion with chaperone modules. *J Mol Biol* 345, 1229-1241

37. Nelson, J. D., Kinkead, H., Brunel, F. M., Leaman, D., Jensen, R., Louis, J. M., Maruyama, T., Bewley, C. A., Bowdish, K., Clore, G. M., Dawson, P. E., Frederickson, S., Mage, R. G., Richman, D. D., Burton, D. R., and Zwick, M. B. (2008) Antibody elicited against the gp41 N-heptad repeat (NHR) coiled-coil can neutralize HIV-1 with modest potency but non-neutralizing antibodies also bind to NHR mimetics. *Virology* 377, 170-183

38. Wang, J., Tong, P., Lu, L., Zhou, L., Xu, L., Jiang, S., and Chen, Y. H. (2011) HIV-1 gp41 core with exposed membrane-proximal external region inducing broad HIV-1 neutralizing antibodies. *PLoS One* 6, e18233

39. Kim, M., Qiao, Z., Yu, J., Montefiori, D., and Reinherz, E. L. (2007) Immunogenicity of recombinant human immunodeficiency virus type 1-like particles expressing gp41 derivatives in a pre-fusion state. *Vaccine* 25, 5102-5114

40. Hager-Braun, C., Katinger, H., and Tomer, K. B. (2006) The HIV-neutralizing monoclonal antibody 4E10 recognizes N-terminal sequences on the native antigen. *J Immunol* 176, 7471-7481

41. Lorizate, M., Gomara, M. J., de la Torre, B. G., Andreu, D., and Nieva, J. L. (2006) Membrane-transferring sequences of the HIV-1 gp41 ectodomain assemble into an immunogenic complex. *J Mol Biol* 360, 45-55

42. Qin, L., Fokine, A., O'Donnell, E., Rao, V. B., and Rossmann, M. G. (2009) Structure of the small outer capsid protein, Soc: a clamp for stabilizing capsids of T4-like phages. *Mol Biol* 395, 728-741

43. Horton, R. M., Hunt, H. D., Ho, S. N., Pullen, J. K., and Pease, L. R. (1989) Engineering hybrid genes without the use of restriction enzymes: gene splicing by overlap extension. *Gene* 77, 61-68

44. Montefiori, D. C. (2009) Measuring HIV neutralization in a luciferase reporter gene assay. *Methods Mol Biol* 485, 395-405

45. Polonis, V. R., Brown, B. K., Rosa Borges, A., Zolla-Pazner, S., Dimitrov, D. S., Zhang, M. Y., Barnett, S. W., Ruprecht, R. M., Scarlatti, G., Fenyo, E. M., Montefiori, D. C., McCutchan, F. E., and Michael, N. L. (2008) Recent advances in the characterization of HIV-1 neutralization assays for standardized evaluation of the antibody response to infection and vaccination. *Virology* 375, 315-320

46. Pancera, M., Majeed, S., Ban, Y. E., Chen, L., Huang, C. C., Kong, L., Kwon, Y. D., Stuckey, J., Zhou, T., Robinson, J. E., Schief, W. R., Sodroski, J., Wyatt, R., and Kwong, P. D. (2010) Structure of HIV-1 gp120 with gp41-interactive region reveals layered envelope architecture and basis of conformational mobility. *Proc Natl Acad Sci USA* 107, 1166-1171

47. Yang, X., Lee, J., Mahony, E. M., Kwong, P. D., Wyatt, R., and Sodroski, J. (2002) Highly stable trimers formed by human immunodeficiency virus type 1 envelope glycoproteins fused with the trimeric motif of T4 bacteriophage fibritin. *J Virol* 76, 4634-4642

48. Li, Q., Shivachandra, S. B., Zhang, Z., and Rao, V. B. (2007) Assembly of the small outer capsid protein, Soc, on bacteriophage T4: a novel system for high density 49. Gnann, J. W., Jr., Nelson, J. A., and Oldstone, M. B. (1987) Fine mapping of an immunodominant domain in the transmembrane glycoprotein of human immunodeficiency virus. *J Virol* 61, 2639-2641
50. Mathiesen, T., Chiodi, F., Broliden, P. A., Albert, J., Houghten, R. A., Utter, G., Wahren, B., and Norrby, E. (1989) Analysis of a subclass-restricted HIV-1 gp41 epitope by omission peptides. *Immunology* 67, 1-7
51. Wang, J. J., Steel, S., Wisniewolski, R., and Wang, C. Y. (1986) Detection of antibodies to human T-lymphotropic virus type III by using a synthetic peptide of 21 amino acid residues corresponding to a highly antigenic segment of gp41 envelope protein. *Proc Natl Acad Sci USA* 83, 6159-6163
52. Robinson, W. E., Jr., Gorny, M. K., Xu, J. Y., Mitchell, W. M., and Zolla-Pazner, S. (1991) Two immunodominant domains of gp41 bind antibodies which enhance human immunodeficiency virus type 1 infection in vitro. *J Virol* 65, 4169-4176
53. Robinson, W. E., Jr., Kawamura, T., Lake, D., Masuho, Y., Mitchell, W. M., and Hersh, E. M. (1990) Antibodies to the primary immunodominant domain of human immunodeficiency virus type 1 (HIV-1) glycoprotein gp41 enhance HIV-1 infection in vitro. *J Virol* 64, 5301-5305
54. Tran, E. E., Borgnia, M. J., Kuybeda, O., Schauder, D. M., Bartesaghi, A., Frank, G. A., Sapiro, G., Milne, J. L., and Subramaniam, S. (2012) Structural Mechanism of Trimeric HIV-1 Envelope Glycoprotein Activation. *PLoS Pathog* 8, e1002797
55. Tsumoto, K., Umetsu, M., Kumagai, I., Ejima, D., Philo, J. S., and Arakawa, T. (2004) Role of arginine in protein refolding, solubilization, and purification. *Biotechnol Prog* 20, 1301-1308
56. Finnegan, C. M., Berg, W., Lewis, G. K., and DeVico, A. L. (2002) Antigenic properties of the human immunodeficiency virus transmembrane glycoprotein during cell-cell fusion. *J Virol* 76, 12123-12134
57. Heitz, F., Morris, M. C., and Divita, G. (2009) Twenty years of cell-penetrating peptides: from molecular mechanisms to therapeutics. *Br J Pharmacol* 157, 195-206
58. Melchers, M., Matthews, K., de Vries, R. P., Eggink, D., van Montfort, T., Bontjer, I., van de Sandt, C., David, K., Berkhout, B., Moore, J. P., and Sanders, R. W. (2011) A stabilized HIV-1 envelope glycoprotein trimer fused to CD40 ligand targets and activates dendritic cells. *Retrovirology* 8, 48
59. Pantophlet, R., and Burton, D. R. (2006) GP120: target for neutralizing HIV-1 antibodies. *Annu Rev Immunol* 24, 739-769
60. Wei, X., Decker, J. M., Wang, S., Hui, H., Kappes, J. C., Wu, X., Salazar-Gonzalez, J. F., Salazar, M. G., Kilby, J. M., Saag, M. S., Komarova, N. L., Nowak, M. A., Hahn, B. H., Kwong, P. D., and Shaw, G. M. (2003) Antibody neutralization and escape by HIV-1. *Nature* 422, 307-312
61. Greenberg, M., Cammack, N., Salgo, M., and Smiley, L. (2004) HIV fusion and its inhibition in antiretroviral therapy. *Rev Med Virol* 14, 321-337
62. Bianchi, E., Joyce, J. G., Miller, M. D., Finnefrock, A. C., Liang, X., Finotto, M., Ingallinella, P., McKenna, P., Citron, M., Ottinger, E., Hepler, R. W., Hrin, R., Nahas, D., Wu, C., Montefiori, D., Shiver, J. W., Pessi, A., and Kim, P. S. (2010) Vaccination with peptide mimetics of the gp41 prehairpin fusion intermediate yields neutralizing antisera against HIV-1 isolates. *Proc Natl Acad Sci USA* 107, 10655-10660
63. Li, Q., Shivachandra, S. B., Leppla, S. H., and Rao, V. B. (2006) Bacteriophage T4 capsid: a unique platform for efficient surface assembly of macromolecular complexes. *J Mol Biol* 363, 577-588
64. Sathaliyawala, T., Rao, M., Maclean, D. M., Birx, D. L., Alving, C. R., and Rao, V. B. (2006) Assembly of human immunodeficiency virus (HIV) antigens on bacteriophage T4: a novel in vitro approach to construct multicomponent HIV vaccines. *J Virol* 80, 7688-7698
65. Peachman, K. K., Li, Q., Matyas, G. R., Shivachandra, S. B., Lovchik, J., Lyons, R. C., Alving, C. R., Rao, V. B., and Rao, M. (2011) Anthrax vaccine antigen-adjuvant formulations completely protect New Zealand white rabbits against challenge with *Bacillus anthracis* Ames strain spores. *Clin Vaccine Immunol* 19, 11-16
66. Barouch, D. H., Liu, J., Li, H., Maxfield, L. F., Abbink, P., Lynch, D. M., Iampietro, M. J., SanMiguel, A., Seaman, M. S., Ferrari, G., Forthal, D. N., Ourmanov, I., Hirsch, V. M., Carville, A., Mansfield, K. G., Stablein, D., Pau, M. G., Schuitemaker, H., Sadoff, J. C., Billings, E. A., Rao, M., Robb, M. L., Kim, J. H., Marovich, M. A., Goudsmit, J., and Michael, N. L. (2012) Vaccine protection against acquisition of neutralization-resistant SIV challenges in rhesus monkeys. *Nature* 482, 89-93

What is claimed is:

1. A method for producing a soluble HIV-1 gp41 recombinant protein comprising:
    isolating an HIV-1 gp41 recombinant protein by affinity chromatography from a supernatant of cell lysate of a cell expressing the HIV-1 gp41 recombinant protein, thereby producing purified soluble HIV-1 gp41 recombinant protein;
    wherein the HIV-1 gp41 recombinant protein comprises an amino acid sequence set forth in SEQ ID NO: 6, and
    wherein the purified soluble HIV-1 gp41 recombinant protein comprises soluble oligomeric HIV-1 gp41 recombinant protein and soluble trimeric HIV-1 gp41 recombinant protein.

2. The method of claim 1 comprising:

separating the soluble trimeric HIV-1 gp41 recombinant protein from the soluble oligomeric HIV-1 gp41 recombinant protein by size exclusion gel filtration chromatography, thereby producing purified soluble trimeric HIV-1 gp41 recombinant protein.

3. A method for producing a soluble HIV-1 gp41 recombinant protein comprising:

isolating an HIV-1 gp41 recombinant protein from an inclusion body fraction of a cell lysate of a cell expressing the HIV-1 gp41 recombinant protein by urea denaturation and affinity chromatography, thereby obtaining isolated soluble HIV-1 gp41 recombinant protein; and refolding the isolated soluble HIV-1 gp41 recombinant protein by slow dialysis against solutions containing incrementally decreased urea concentration, thereby producing refolded soluble HIV-1 gp41 recombinant protein;

wherein the HIV-1 gp41 recombinant protein comprises an amino acid sequence set forth in SEQ ID NO: 6, and wherein the refolded soluble HIV-1 gp41 recombinant protein comprises soluble oligomeric HIV-1 gp41 recombinant protein and soluble trimeric HIV-1 gp41 recombinant protein.

4. The method of claim 3 comprising:

separating the soluble trimeric HIV-1 gp41 recombinant protein from the soluble oligomeric HIV-1 gp41 recombinant protein by size exclusion gel filtration chromatography, thereby producing purified soluble trimeric HIV-1 gp41 recombinant protein.

5. A method for expressing a soluble HIV-1 gp41 recombinant protein comprising inducing an expression of an HIV-1 gp41 recombinant protein comprising SEQ ID NO: 6 in a cell, wherein the cell contains an expression vector comprising a DNA fragment encoding the HIV-1 gp41 recombinant protein comprising SEQ ID NO: 6.

* * * * *

UNITED STATES PATENT AND TRADEMARK OFFICE
CERTIFICATE OF CORRECTION

| | |
|---|---|
| PATENT NO. | : 9,701,722 B2 |
| APPLICATION NO. | : 15/080804 |
| DATED | : July 11, 2017 |
| INVENTOR(S) | : Venigalla B. Rao et al. |

It is certified that error appears in the above-identified patent and that said Letters Patent is hereby corrected as shown below:

In the Specification

Column 1, Line 22 insert --STATEMENT OF GOVERNMENT INTEREST
This invention was made with government support under Grant No. AI102725 awarded by the National Institutes of Health. The government has certain rights in the invention.--

Signed and Sealed this
Eighteenth Day of June, 2019

Andrei Iancu
*Director of the United States Patent and Trademark Office*